(12) United States Patent
Robbins et al.

(10) Patent No.: US 11,728,016 B2
(45) Date of Patent: Aug. 15, 2023

(54) METHOD AND SYSTEM FOR CAPTURING PERSON CENTERED HEALTHCARE DATA, USING A BUFFER TO TEMPORARILY STORE THE DATA FOR ANALYSIS, AND STORING THE DATA WITHOUT DELETION, INCLUDING GOAL, OUTCOME, AND MEDICATION ERROR DATA

(71) Applicant: Therap Services, LLC, Waterbury, CT (US)

(72) Inventors: Richard Allen Robbins, New York, NY (US); Justin Mark Brockie, Wolcot, CT (US); James Kelly, Woodbury, CT (US); David Turock, Lauderdale by the Sea, FL (US)

(73) Assignee: Therap Services, LLC, Torrington, CT (US)

( * ) Notice: Subject to any disclaimer, the term of this patent is extended or adjusted under 35 U.S.C. 154(b) by 41 days.

(21) Appl. No.: 17/566,202

(22) Filed: Dec. 30, 2021

(65) Prior Publication Data
US 2022/0122704 A1 Apr. 21, 2022

Related U.S. Application Data

(60) Continuation of application No. 16/811,429, filed on Mar. 6, 2020, now Pat. No. 11,410,759, which is a
(Continued)

(51) Int. Cl.
*G16H 10/60* (2018.01)
*G06F 12/0888* (2016.01)
(Continued)

(52) U.S. Cl.
CPC ......... *G16H 10/60* (2018.01); *G06F 12/0888* (2013.01); *G16H 15/00* (2018.01);
(Continued)

(58) Field of Classification Search
CPC ........ G16H 10/60; G16H 40/67; G16H 15/00; G16H 30/20; G06F 12/0888; G06F 2212/45
(Continued)

(56) References Cited

U.S. PATENT DOCUMENTS

2005/0115561 A1* 6/2005 Stahmann .......... A61B 5/02055
128/204.23
2006/0009942 A1* 1/2006 Keck ...................... G06Q 50/04
702/122
(Continued)

*Primary Examiner* — Michael Tomaszewski
(74) *Attorney, Agent, or Firm* — Hughes Hubbard & Reed LLP

(57) ABSTRACT

A system and method for recording healthcare information of an individual under care without deleting data, includes a device for capturing person centered data and transmitting an identification signal, a memory for storing device rules, a buffer, a database; and a processor. The processor receives the signal and data, and retrieves the rules from the memory. Based on the rules, the processor determines whether the data is to be stored in the database or the buffer, and based on the data content, it determines the device location, the data recordation time, whether the individual is identified, and the individual's activity, and based on the rules and the location, time, individual identification, and activity, it determines whether the data is to be stored in the database or eliminated from the buffer. The person-centered data may include goal, outcome, medication error data, non-person centered public data, or protected health information (PHI).

20 Claims, 46 Drawing Sheets

Related U.S. Application Data continuation of application No. 15/636,826, filed on Jun. 29, 2017, now Pat. No. 10,622,103, which is a continuation-in-part of application No. 13/675,440, filed on Nov. 13, 2012, now abandoned, said application No. 13/600,388 is a continuation-in-part of application No. 13/600,402, filed on Aug. 31, 2012, now Pat. No. 8,613,054, said application No. 13/675, 440 is a continuation-in-part of application No. 13/600,388, filed on Aug. 31, 2012, now Pat. No. 8,615,790, said application No. 13/600,402 is a division of application No. 11/604,577, filed on Nov. 27, 2006, now Pat. No. 8,281,370.

(51) Int. Cl.
*G16H 40/67* (2018.01)
*G16H 15/00* (2018.01)
*G16H 30/20* (2018.01)

(52) U.S. Cl.
CPC ......... *G16H 40/67* (2018.01); *G06F 2212/45* (2013.01); *G16H 30/20* (2018.01)

(58) Field of Classification Search
USPC ........................................................ 705/2–3
See application file for complete search history.

(56) References Cited

U.S. PATENT DOCUMENTS

| | | | |
|---|---|---|---|
| 2014/0046695 A1* | 2/2014 | Meyer | G16H 10/60 705/3 |
| 2015/0378921 A1* | 12/2015 | Karippara | G06F 9/45533 710/308 |
| 2016/0300016 A1* | 10/2016 | Dominick | G06F 16/214 |
| 2018/0095882 A1* | 4/2018 | Wilkins | G06F 12/084 |

* cited by examiner

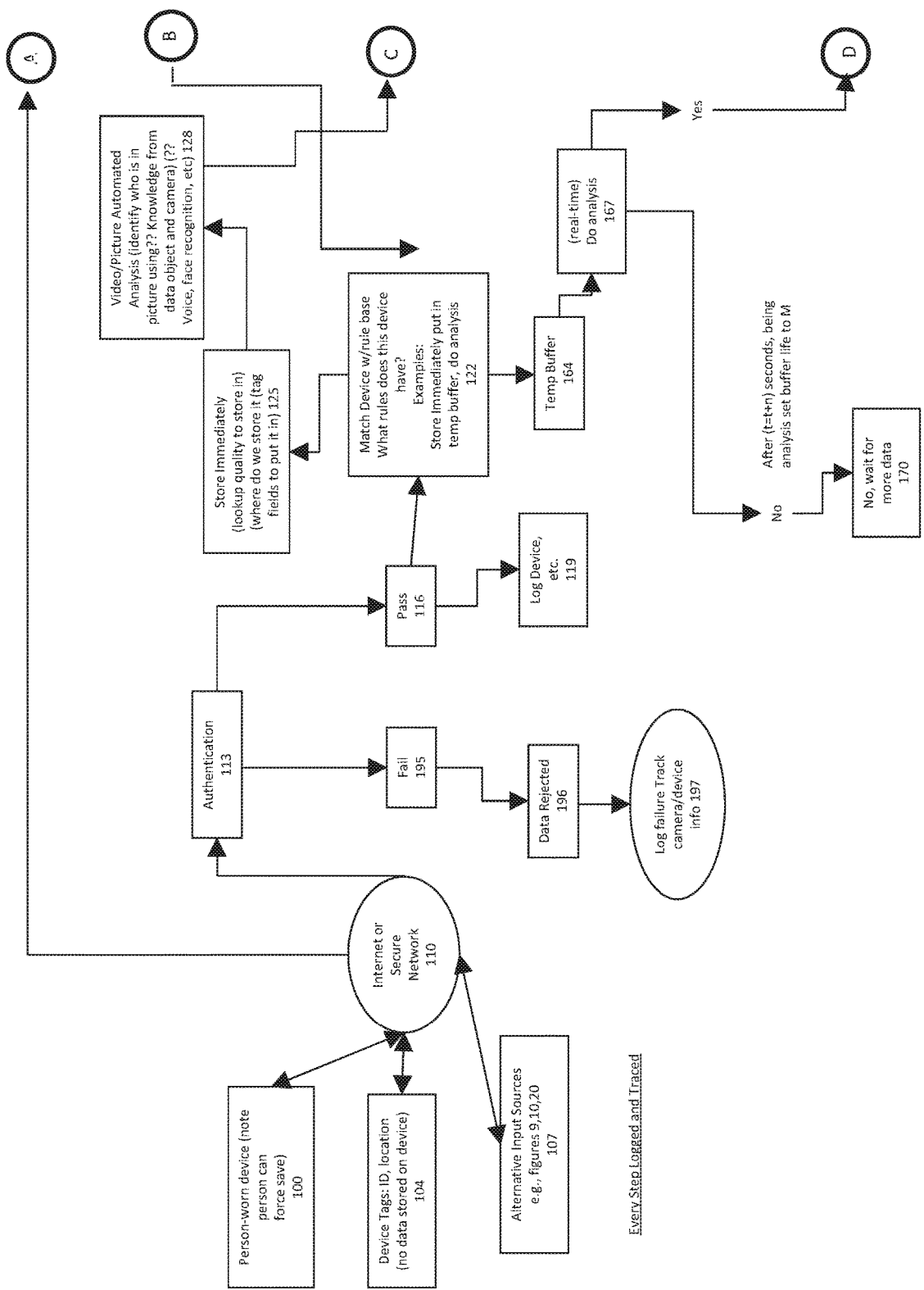

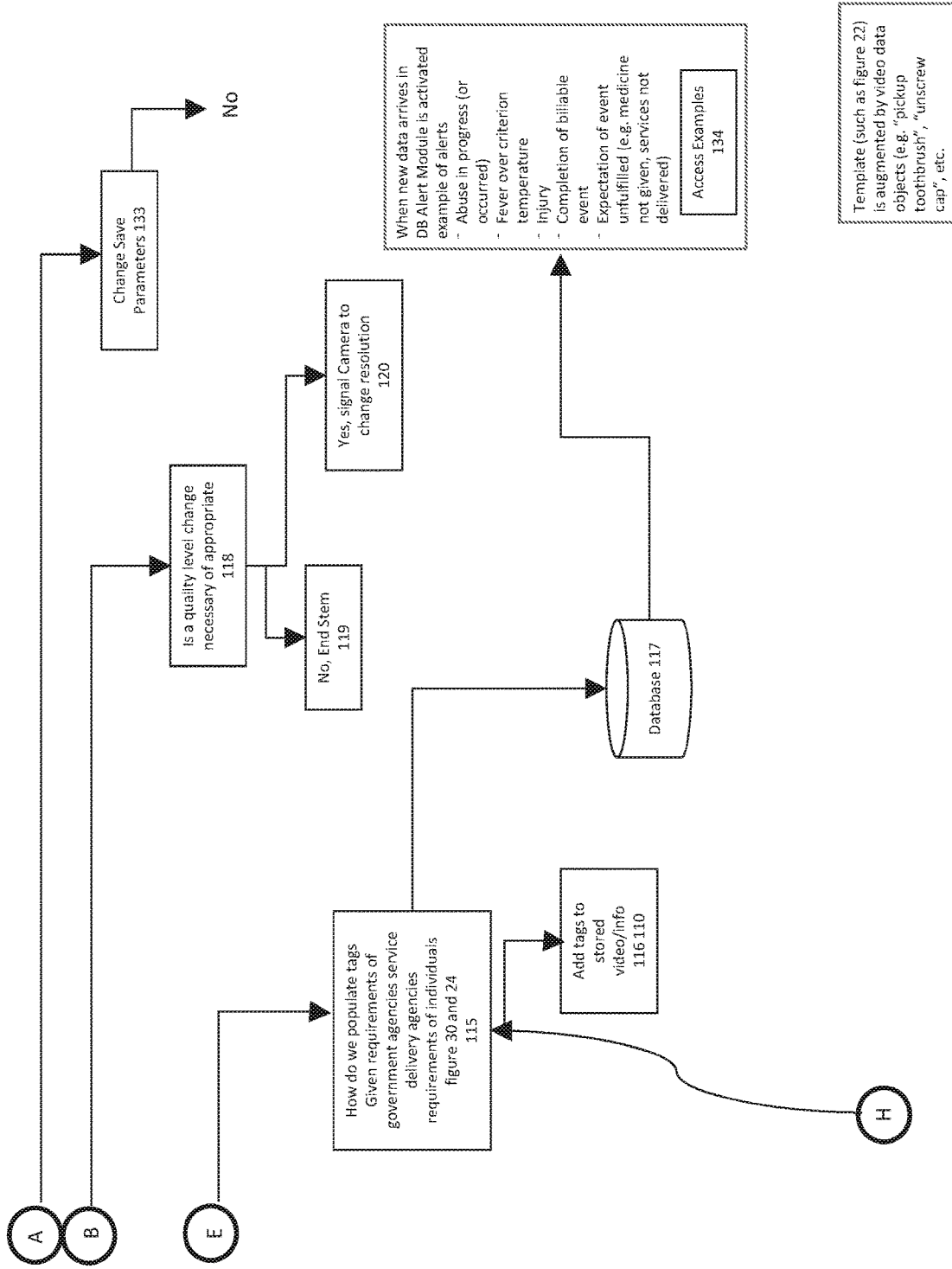

Figure 8

| List of range of Methods and qualities of Storage 121 | |
|---|---|
| HD 311<br>Quality 2  312<br>Quality 3  313<br>Low Quality Video 314<br>High Resolution Picture 315<br>Low Resolution Picture 316<br>Audio 316<br>partially redacted images | |

Activity Tracking Regarding Temporary Data

An Example of Device Capturing Information

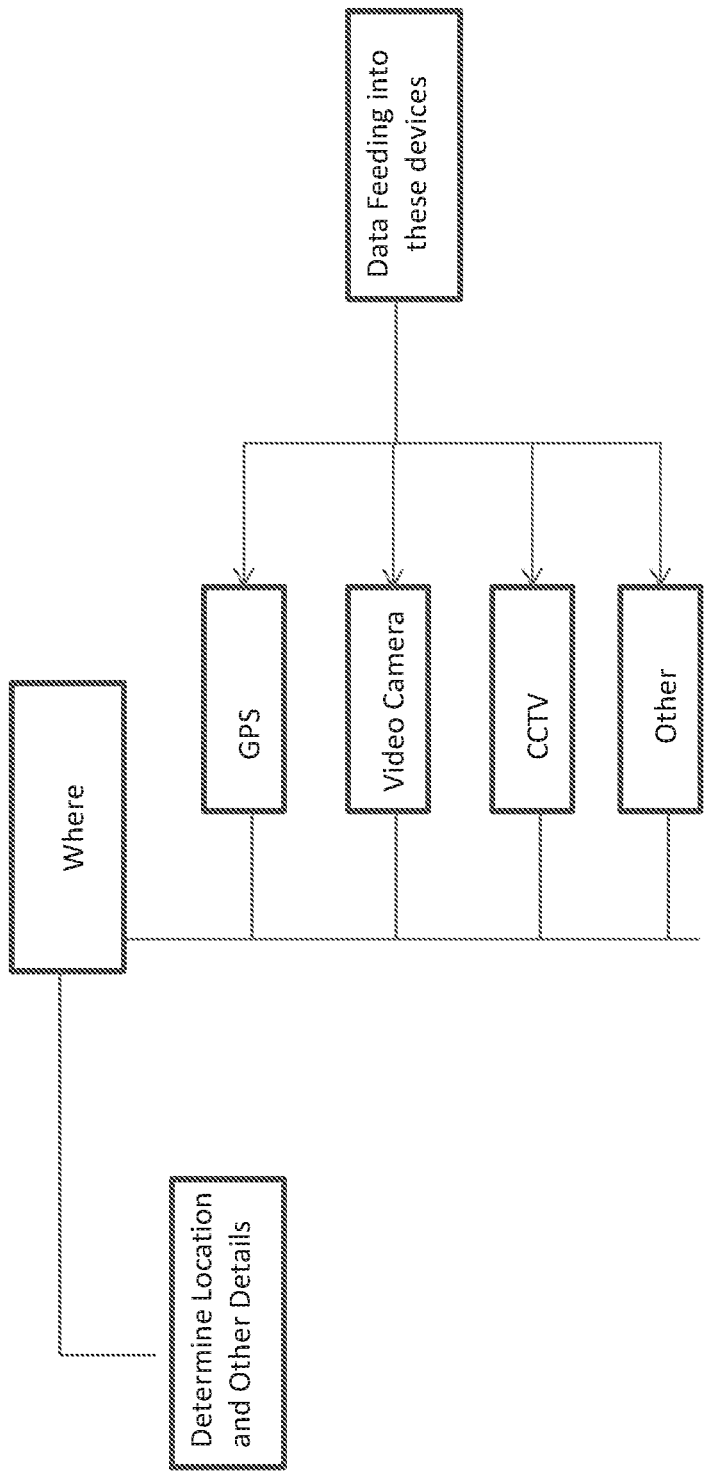

Figure 20

Methods of Identifying People in the video 131

Voice 411
Biometrics 412
Previous Logs 413
Biometrics match 414
Verbal Password 415
Location Helping 416
Cannot Identify 417
Guess on Person 418
Can always mark wrong person later 419
human assistance in identification 420
combination of methods 421
other methods 422
knowledge of staff, families and individuals who are in a specific location 423

Forms with Data collected by system

Determine Documentation and Analysis Field Requirements

Data Collected for Analysis for Funding Agencies

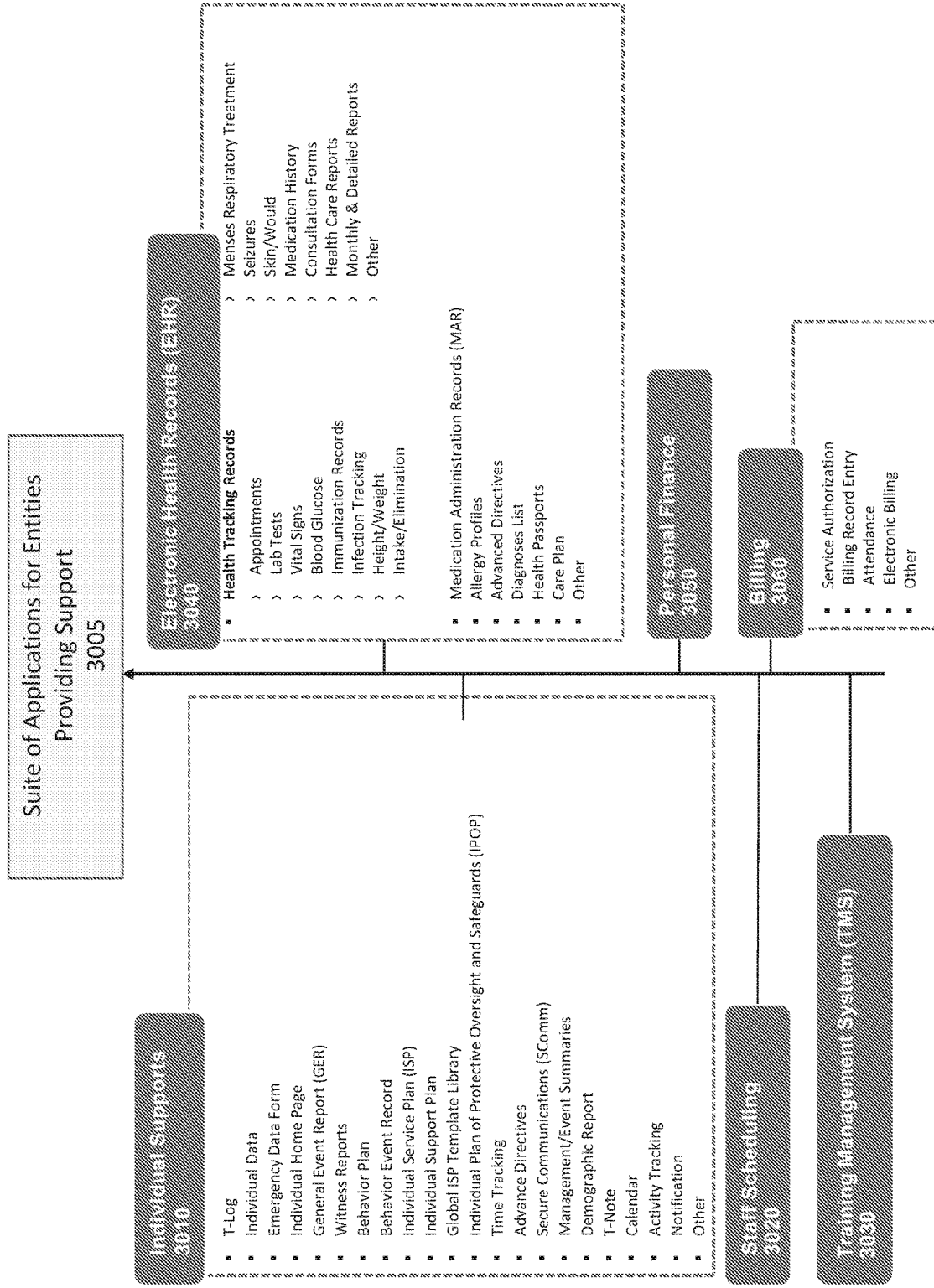

Determining Caseloads for Multiple Individuals in Data

METHOD AND SYSTEM FOR CAPTURING PERSON CENTERED HEALTHCARE DATA, USING A BUFFER TO TEMPORARILY STORE THE DATA FOR ANALYSIS, AND STORING THE DATA WITHOUT DELETION, INCLUDING GOAL, OUTCOME, AND MEDICATION ERROR DATA

RELATED APPLICATIONS

This application is a continuation of U.S. patent application Ser. No. 16/811,429, filed Mar. 4, 2020, which is a continuation of U.S. Pat. No. 10,622,103 filed as U.S. patent application Ser. No. 15/636,826 on Jun. 29, 2017 and issued Apr. 14, 2020, which is a continuation-in-part of U.S. patent application Ser. No. 13/675,440 filed Nov. 13, 2012, which is a continuation-in-part of U.S. Pat. No. 8,615,790 filed as U.S. patent application Ser. No. 13/600,388 on Aug. 31, 2012 and issued Dec. 24, 2013, which is a continuation-in-part of U.S. Pat. No. 8,613,054 filed as U.S. patent application Ser. No. 13/600,402 on Aug. 31, 2012 and issued Dec. 17, 2013, which is a division of U.S. Pat. No. 8,281,370 filed as U.S. patent application Ser. No. 11/604,557 on Nov. 27, 2006 and issued Oct. 2, 2012, the disclosures and teachings of all of which are incorporated herein by reference.

FIELD OF THE INVENTION

The present invention relates to methods and systems for acquiring, processing and storing information collected from individuals and for deciding quality and quantity of video to save based on properties of the video content and other individual-centered rules.

BACKGROUND OF THE INVENTION AND DISCLOSURE

A goal of human service agencies may be to have more person centered documentation of events in an individual's life. The documentation may contain video, audio, or sensor telemetry of events.

There may be a need to not delete stored data to preserve data integrity. This may be a particular issue with Protected Health Information (PHI) or other information required for compliance with federal or government regulations.

Having video of an actual situation related to a person may be a key component for person centered documentation. For individuals with intellectual or cognitive disabilities who are receiving support from others there is a challenge to make sure that their goals and opinions are properly represented. There is also a need to make sure that once data is stored it is not selectively deleted. In many cases these individuals are receiving support from multiple agencies with multiple oversights and monitoring organizations.

In applications requiring proof of positive or negative individual satisfaction, proof of service delivery, time, location and meeting individual goals for people with intellectual and/or cognitive disabilities who have guardians and or funded caregivers, or monitored by funding agencies, the state of the art is paper or text based documentation perhaps with some photographs attached. A significant feature of laws such as HIPAA is the maintenance of a documentation trail of who has seen pieces of information, where the information came from and the non-destruction of PHI once information is saved. This may be a problem for video, audio, sensor and other documentation.

Multiple cameras with up to 24 hour by 7 day a week high definition, 3D or other high quality storage may be quite expensive to maintain. There could be many hours of storage where either nothing has occurred or nothing perceived as significant has occurred. In certain instances, perhaps with abuse and neglect, what is significant may be determined based on what occurred subsequently.

Movable cameras, such as those attached to a gyroscopic robot device may also be used to follow and monitor an individual during the course of his or her day.

If video regarding an individual is saved, that information may not be able to be deleted based on law or a concern about the loss of data integrity of other data and video in a documentation system. If video is saved in a high quality format which is not needed for documentation this may become costly in terms of storage costs and difficult in terms of managing a large amount of video files. If video is not saved in high quality formats then key information might be missing to make video taken of certain medical or abuse situations unusable or unenforceable.

Typically proof of service delivery, individual satisfaction of service provided and achievement of individual goals is documented using either paper or electronic formats. The desired information is entered on paper forms or some form of electronic database. These methods are prone to information which does not accurately reflect what happened. Someone might misremember all details of event either intentionally or unintentionally. There may be space limits on space in certain forms. Something might have occurred when no one was around to see what occurred. Something might have been observed by someone without the verbal or cognitive capability to fully describe what occurred. Someone might be describing something in a manner to cover up what actually occurred. There might be two or more people with different interpretations of what occurred. Video documentation could reduce or eliminate many of these problems.

Different staff, consultants, family members and others may either inaccurately interpret or falsely document information about an individual's satisfaction, achievement or additional responses. These are challenges with the current system of static dropdown choices answers, rating systems or defined check boxes to questions.

In addition, organizations providing these services work with significant budgetary issues. While most agencies work hard to provide excellent services, there are some agencies which do not have the same reputation, service quality or training and it is important to be able to have accurate documentation of service delivery and achievement of goals. It is a challenge for people with intellectual and/or cognitive disabilities to have accurate reporting on the achievement of goals, satisfaction of service received, or potential problems such as abuse and neglect.

There may also be situations where staff may be accused of abuse and neglect or not performing certain tasks. By having a rules based video saving system staff can have video and other documentation to help prove either the absence of wrong activity or the positive provision of proper services. There are many staff and family members accused of wrongdoing which has financial and reputational consequences which this process could avoid.

There are many current, significant issues with the prevention of abuse and neglect of individuals in this country receiving healthcare services. Having documentation by the same staff, consultants, or family of who might be causing the abuse and neglect is not as optimal as having the video showing the care, services and relationships. This need for accurately recording these activities is a challenge with paper based documentation—the current standard in the industry—when it cannot be independently filled out and submitted by a person who is the subject of the documentation. It can also be a challenge when a staff can video an individual and then submit that video after the fact depending on the answer given. This presents constant oversight of all treatment, both positive and negative, and has the potential to result in only the documentation of positive results, thus blanketing any negative issues from coming to light.

There are issues where different agencies, individuals, staff, funding agencies, guardians or others may have documentation goals or requirements which are not known to a staff member or other person providing service or support to an individual. These could relate to issues ranging from proof of service delivery for funding reimbursement to monitoring staff for potential abuse and neglect to individual person centered goals to medication and behavioral conditions. A broader real time interpretation of data in a person's files across multiple caseloads and roles of access could provide a changed requirement for data and video to be stored.

The proposed solution provides a method for saving and storing data without permitting any deletion or destruction of data after data is saved. Video or audio are processed by a range of input devices including direct connection of a camera, phone, pc, smartphone, mobile device or other device connected securely to a central physical location over the internet or equivalent. Video or audio regarding the target individual would preferably be transferred with a secure connection and analyzed before being stored and saved.

Once data is saved it could be in the system for a minimum of a preset period or number of years without the ability of any user to delete or destroy the data. This would create an audit trail and integrity to the data.

The data would be able to be accessed by individuals or staff based on caseloads and roles related to individuals in the video as well as actions which have occurred. The system could automatically determine these access levels based on interpretation of events in the video. The system could determine who is in the video based on a variety of factors including biometrics, passwords, rolling key encryption, secure access cards, etc. The system might not need to know who is in the system to make a decision on whether and in what format to save. For example the system might only have data on someone brushing their teeth if it was part of an individual plan and noted to be saved in video for a given individual, however if there were evidence of abuse or violence the system could have rules to save video if certain events occurred even without knowing the individuals in the video.

The system would have the ability to tag or change tags on individuals subsequent to the saving of the video. The system would document the various individuals ascribed to be in the video. These would be logged and tracked for future audit or review.

Documentation is particularly challenging for individuals with intellectual, cognitive, and developmental disabilities, which could be lifelong or temporary conditions with varying degrees of impairments. Individuals may have more emergencies and also be subject to more instances of abuse and neglect. They also may require daily documentation of goals, tasks and objectives. Agencies providing these services may only get paid upon proof of service delivery and satisfaction by the individual. Government or other funding agencies often question activities and withhold or reduce funding because of questionable documentation of activities or because documentation was not done co-terminally with the provision of services.

Certain religious members have a particular problem because of provisions of writing or using electronic devices during certain holidays or other periods. This system would permit information to be saved and then additional analysis provided later after the religious observance.

Access to Personal Health Information ("PHI") about health and related conditions is strictly regulated by the Health Insurance Portability and Accountability Act of 1996 ("HIPAA"), the American Recovery and Reinvestment Act of 2009 ("ARRA"), and Health Information Technology for Economic and Clinical Health Act ("HITECH") and other state and federal regulations which complicates providing support and services including analyzing and reviewing documentation.

In addition funding and reimbursement regulations are set by state, county and other government agencies as well as non-profit and for-profit organizations. These regulations can provide specific requirements for activities to occur in order to receive reimbursement. The system can be configured to ensure that all processing of data is consistent with these and other requirements.

The issues here are not only related to people with cognitive disabilities. There have been instances or allegations of abuse and neglect by teachers, coaches, job supervisors or others in general society. This system can provide a method to help provide either the occurrence or non-occurrence of any activity that can be recognized by the system.

This method allows for notification to staff or others based on caseloads and super roles and based on the event which actually occurred. Only people who would have access to an individual and to the type of information based on the information in the video would have access to see all or a portion of the video as appropriate.

This method allows for the situation where different staff members observe an individual doing the same action or responding in a certain way and each staff member might interpret that information and document it differently. Given that an individual might have a lifelong condition and staff members can be transitory and thus have limited information, there exists a problem with the information flow available to a staff member. Because documentation is being saved and analyzed from video information there is less staff interpretation of actual facts.

This method allows the checking of requirements on how to save video (after it is in a temporary condition but not yet saved) against individuals plans, person centered goals, previous notes and documentation in the system, staffing issues, and other data requirements. Where a pre-specified set of criteria are met, then temporary data can be moved to a more permanent store, as required.

In the face of such challenges it becomes difficult for care providers to both ensure satisfaction of service provided to the individual and proof of service delivery provided to an individual.

Similar situations exist in other industries. Situations with other cognitive impairments which might affect driving or other actions might need to be interpreted based on the individuals intent and capabilities.

Information can be generated from a video, tactile, thermal, electrochemical sensor, body worn sensors or audio capture system (including phones, computers, and other commercially available devices). The information is preferably captured and generated in real time. This eliminates the ability of a staff member to edit or only upload data which generates desired responses.

If potential for abuse and neglect is determined a specified subset of people based on caseloads and defined access roles, called super roles may view information as appropriate to review the situation. One benefit of the system is that the system can look for abuse and neglect across multiple caseloads and super roles based on predetermined rules.

Other potential applications for this automated processing include, but are not limited to, monitoring of public facilities such as train stations, malls, and airports; monitoring of private spaces such as houses, apartments; monitoring of secure areas such as offices and operations centers; monitoring of roadways and traffic patterns on those roadways, and others. Essentially any place where activity may be recorded and analyzed by automated means according to a defined set of rules.

Because the invention includes an intermediate buffer between a healthcare data-capturing device and the memory for storage of that data, the invention represents an improvement in computer technology as well as an improvement in the way computers are used to process electronic healthcare data. Furthermore, no conventional electronic healthcare data includes a rule-based way of determining, prior to storage, whether the data should or is required to be stored.

BRIEF DESCRIPTION OF THE DRAWINGS

FIG. 1A illustrates a first portion of an overview of the embodiments of the system and method of the present invention.

FIG. 1D illustrates a fourth portion, continuing from FIGS. 1A, 1B, and 1C, of an overview of the embodiments of the system and method of the present invention.

FIG. 8 illustrates a list of range of methods and qualities of storage that may be used in embodiments of the system and method of the present invention.

FIG. 19A illustrates aspects of the analysis of where data was recorded.

FIG. 20 illustrates methods of identifying people in a video that may be used in embodiments of the system and method of the present invention.

FIG. 36 illustrates a suite of applications for entities providing support that may be included in embodiments of the system and method of the present invention.

DETAILED DESCRIPTION AND PREFERRED EMBODIMENTS

Figure 1B:
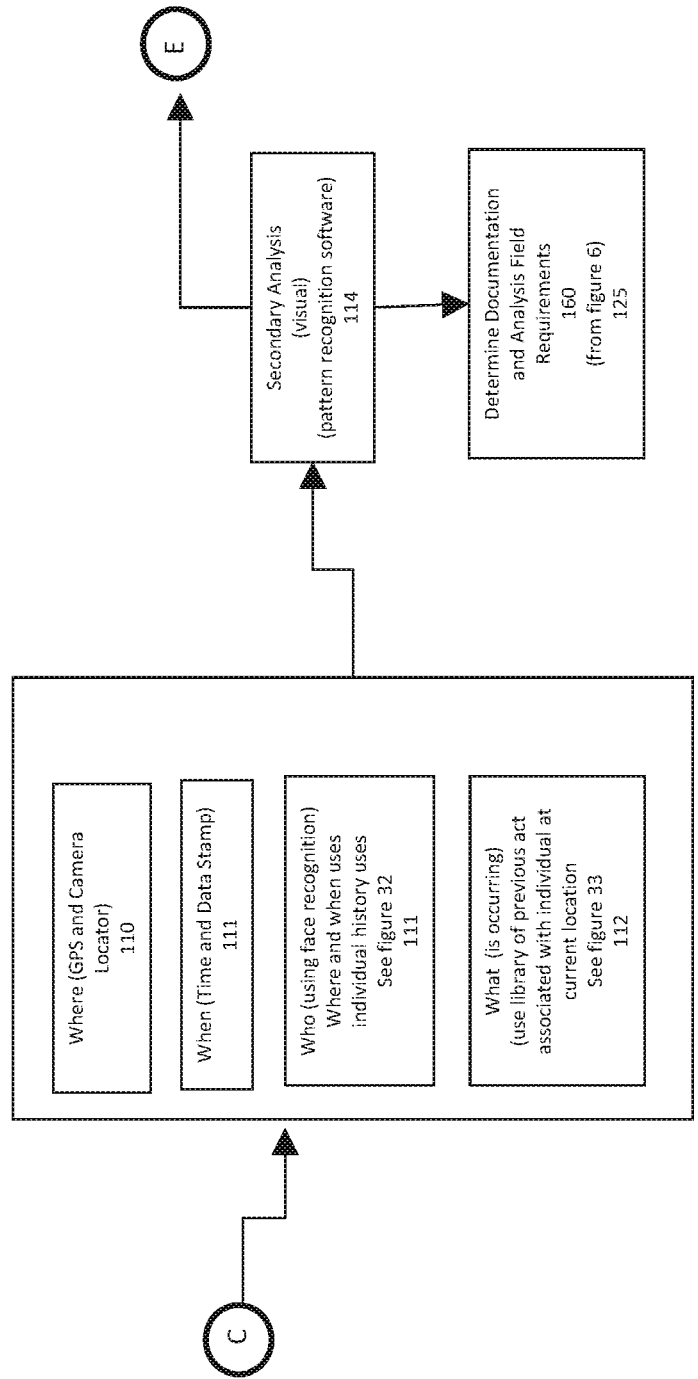
FIG. 1B illustrates a second portion, continuing from FIG. 1A, of an overview of the embodiments of the system and method of the present invention.
Figure 1C:
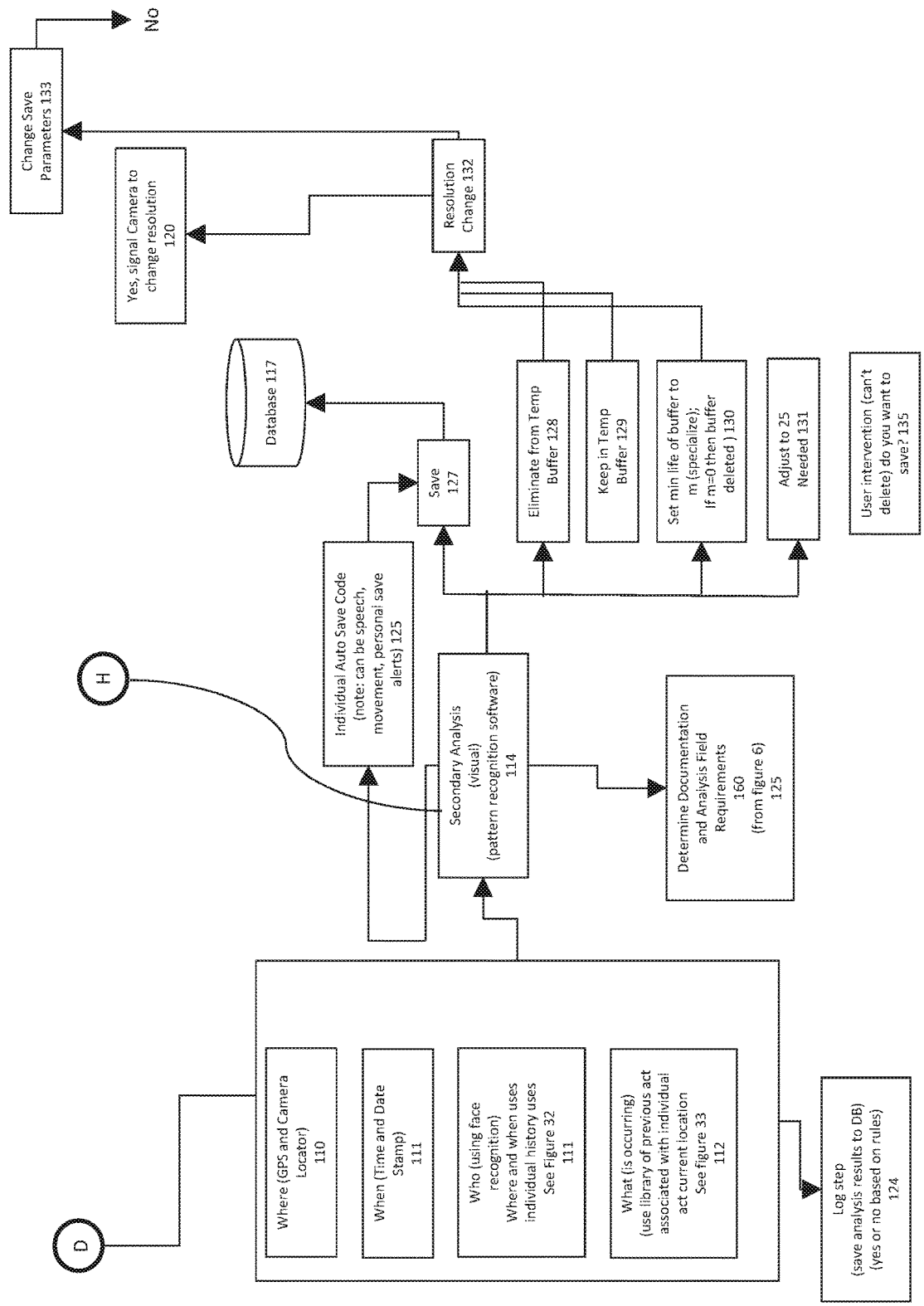
FIG. 1C illustrates a third portion, continuing from FIG. 1A, of an overview of the embodiments of the system and method of the present invention.

Description will now be given of the currently preferred embodiment of the invention with reference to the attached FIGS. 1-38. It should be understood that these figures are exemplary in nature and in no way serve to limit the scope of the invention as the invention will be defined by claims, and the scope of the invention will be the scope of the claims, as interpreted by the Courts.

Introduction

The present invention provides a system for Acquiring, Evaluating, Saving and Storing Video and Data Objects for Individuals without deleting data or other information. The data may need to be shared among multiple security domains or caseloads. This may be of particular benefit for people with cognitive disabilities. Embodiments of this invention may have applications for reporting proof of service delivery and other person centered documentation by people with cognitive disabilities in compliance with PHI across and within organizations in the cognitive disability field in compliance with HIPAA and other regulations and security procedures.

Embodiments of this system ensure that individual information is securely stored, thus eliminating the risk of loss of information as well as tampering or deleting information.

The system allows users to directly store information regarding an individual with cognitive disabilities directly into a database with no risk of selective deletion of data. This information may then be stored for audit integrity.

Individuals or people providing support to individuals with developmental disabilities may choose to have high quality video or other recording of events or activities which have occurred. These agencies may choose to have multiple camera angles or multiple methods of collecting this information. Without a system such as this invention, the cost of maintaining multiple views and cameras without deletion might be cost prohibitive or if deletions were to occur could present problems for government and auditing regulations including HIPAA.

This system will also allow information to be saved which may later be reviewed or analyzed against future documentation to see if a response should be considered differently based on additional information. Because the initial response is stored securely in the system, what is changing is not the actual response but the interpretation of the response, so the documentation is still being recorded in real time as close to the point of delivery and occurrence as possible.

Overview

FIGS. 1A-1D illustrate an overview of the embodiments of the present invention system. Embodiments of the present invention require a number of steps in order to fully grasp, obtain, and understand the information sought.

Data may be collected from different input devices. These devices may include a Person-Worn Device 100, a Device 104 or Alternate Input Sources 107. These devices might not store data on the devices. They are connected to the system through the internet or secure network 108.

After data is received there is an authentication 113 process. Unless a specific device has a code to access system it is not permitted to send any information to the system as the system does not recognize the device. This authentication is checking that the devices are acceptable to send information into the system. At this point the actual data may not be what is being authenticated. So for example the system has to recognize that the Devices connected to the internet are eligible to send data to the system. These steps are logged and tracked 119. So data from a given Device which was a fail 195 in the authentication process still has information which might include time, date, IP address, camera information, quality of video, sensors and other information logged and tracked in the system. The system might not be storing or analyzing what that data was as part of the tracking and logging. Data which was failed is rejected 196. This information is tracked and logged in the system.

If the authentication 113 was a pass 116 then the system tracks and logs basic information about the device, camera, time, IP address, and other information 119.

The system then matches a rule base for that device 122. The system has not yet stored or looked at specific information about the video or other data objects. The system analyzes the rule base given the device. At that point data is either placed in a Temp Buffer 164 which is a temporary condition which is not saved to a permanent storage solution or would be stored immediately 125.

The system then looks to see if an analysis should be performed. The first time data is received from a specific Person-worn device, Device or Alternative Input Source an analysis occurs on when to do the analysis. For example, if there is a video feed, there is not a continuous analysis on the stream of data. There is an initial setting of "N" seconds which could be set by either a rule for the device or by the system default if there is no device rule for when an initial analysis should occur 167. If the initial data is set for 10 seconds then an analysis might not occur until after there was 10 seconds of data from the device. "T" could be set to equal the time since the last analysis of the data from the device. If T is less than N which would mean that the time since the last buffer is less than the interval for analysis then the system would wait for more data 170. If T is greater than N, then an analysis occurs.

In one embodiment, the first part of the analysis is finding out Who 111, What 112, When 111, and Where 110 regarding the actual data. At this point the system could be looking at the video or audio or sensor data. The system tracks and logs the analysis it is doing. The system would not be storing the actual raw data objects but the type of analysis it was doing and the rules it was looking at. The system could log where the data was from, who was in the video, when the data was created and what occurred.

After the systems determines as much as possible of Who, What, Where, and When, the system will apply a Secondary Analysis 114 of this data against rules in its system. The rules may include Documentation and Analysis Field Requirements 125. These requirements may be based on government regulations, agency requirements, person centered goals and objectives or other types of analysis and rules which might impact data needs.

Depending on the Analysis 114 as compared with the information of Who, What, When and Where and with the Document and analysis field requirements a determination may be made by the system to Save 127 the data to permanent storage, to eliminate from Temp Buffer 128 or Keep in Temp Buffer 129. Each step and action is tracked and logged. Any data saved is saved to a system database 117.

The system could also determine that the buffer "M" should be reset to a different time. In one embodiment a user requests the system to save the data. In another a user does not have the ability to cause the system to not save data 135. Data which is saved may need the system to determine what had occurred and populate tags 115 based on requirements of various Documentation and Analysis Field Requirements 115.

In situations where the rules on the match device 122 said to store immediately 125 then the system goes through a video/data automated analysis 128 to determine Where 110, What 112, When 111 and Who 111. The system analyzes the data 114 to determine how to populate tags 115. The system then as appropriate adds tags to stored video/data 116. The data is stored in a database 117.

As shown in FIGS. 1A-1D, Person Controlled Device 100 or Alternate Input Sources 107 transmits data over the Internet or Secure Network 110 to a Temporary Buffer 164 or Save Immediately 125 after Authentication 113.

Figure 3:
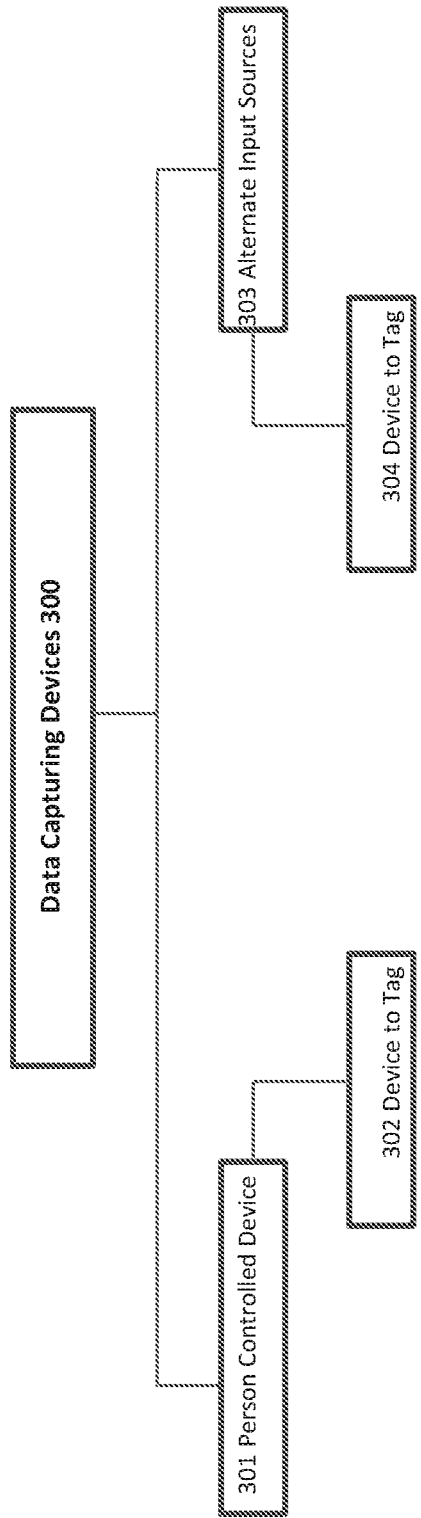
FIG. 3 illustrates types of data capturing devices with multiple feeds or multiple streams that may be used in embodiments of the system and method of the present invention.
Figure 4:
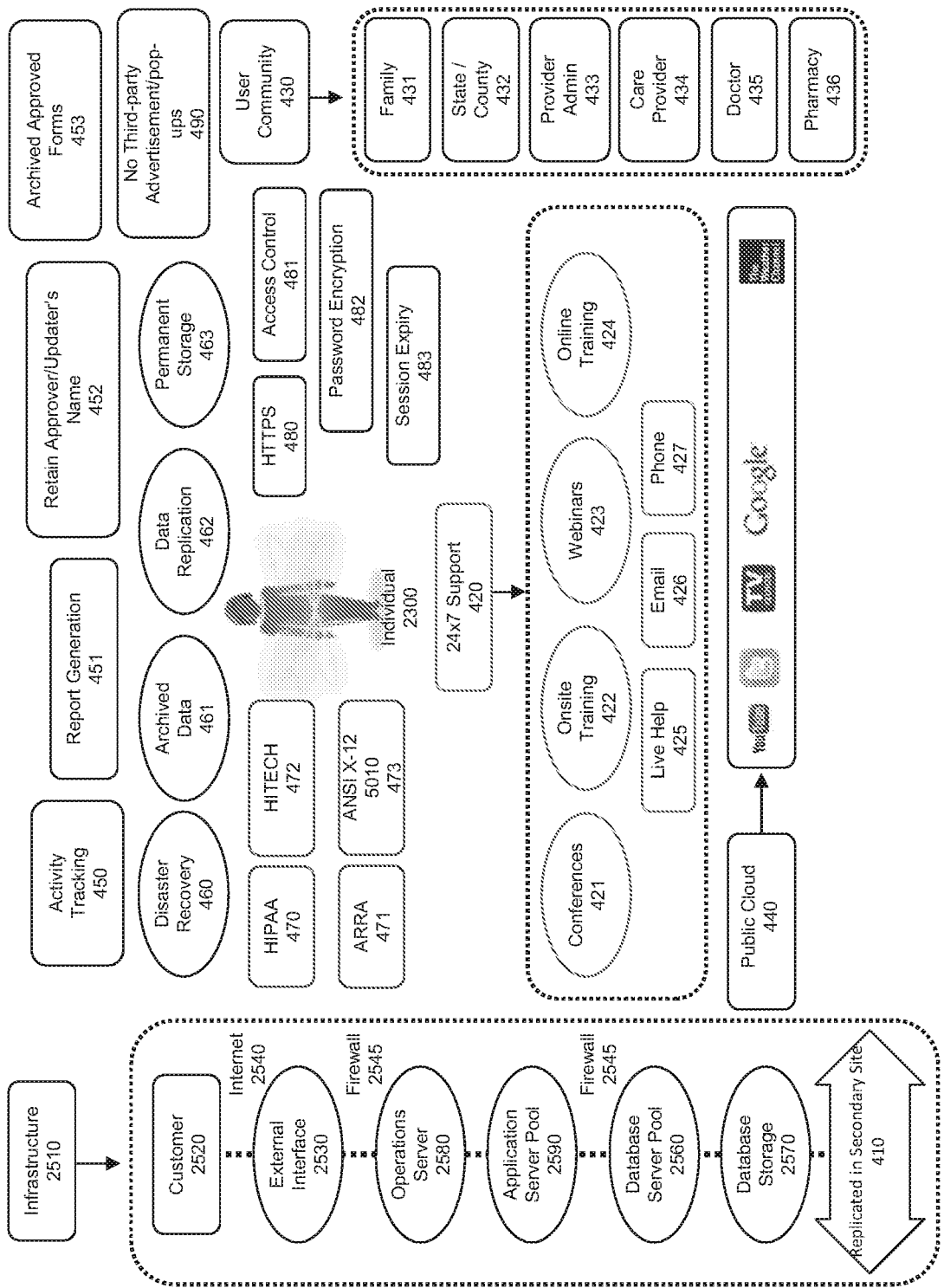
FIG. 4 illustrates an overview of a service provider environment relating to an individual under care.

FIG. 3 identifies types of data capturing devices 300 which may either be Person Controlled 301 or Alternative Input Sources 303. When the information is collected, the device is automatically tracked by the system by the Unique Identifier, IP Address, GPS Location, and other methods. The system would be equipped with a Library of Devices. The device may be tracked by referencing the library of devices, which adds new devices to the library based on a Supervised Learning algorithm. The library of devices and their tracking detail may be incorporated with a machine learning algorithm, i.e. artificial intelligence, to automatically populate more devise into the existing list.

An agency, individual, guardian, government entity or other involved entity might have an interest in having video and other data including audio, 3D, sensory or other accurate account of events.

The initial setup for an agency is by the provider administrator in an embodiment. A provider administrator is a person created by the organization which establishes the account. An agency or person first sets up an account and access roles. The agency receives a provider code which gives access to the system. The provider administrator has signed HIPAA and other user agreements with the system. The provider administrator gives access to people and devices to have access into the system.

A provider administrator sets up roles and access to the system. An agency would establish a list of individuals for whom documentation is being created for as well as staff, families and individuals with access to enter, view, approve and take other actions with respect to that data. A provider administrator also has access to give access to devices to gain access to the data in the system. A provider administrator has one or more passwords or codes which gains access to the system.

Information may be collected using a Person Controlled Device 100 or Alternative Input Sources 107. The list of devices shown in FIG. 2 includes a camera 210, audio 211, sensors 212, biometrics 214, brainwave monitoring 215, cellphone 216, and other input devices 213. An Unmanned specific Device indicates a device which is not controlled by a person but is remotely programmed or controlled by the system. The access to this device would be controlled by a provider administrator or other person with a system role. The initial setup of the roles for the device is created remotely. The device may be any type of camera, video, sensor or other device which may be connected to the system. The unmanned specific device is a specific device which submits data to the system. There may be multiple specific devices in different locations. In fact, there may be multiple specific devices in a nearby location. The device is determined by the method of providing instructions from the system to the device as well as by the flow of data from the device to the system. It is possible that a single piece of equipment may function as two separate unmanned specific devices if there were multiple feeds of instructions to and data from the device. The unmanned specific device may initially be turned on by a provider administrator providing a code to access system to the device and also letting the system know that this is an approved device which may send information to the system.

A person with Device is a person controlling a device as opposed to a device independently connected to the internet or the system without a person near it. A person may walk around with the device or be using it in one location.

Figure 26:
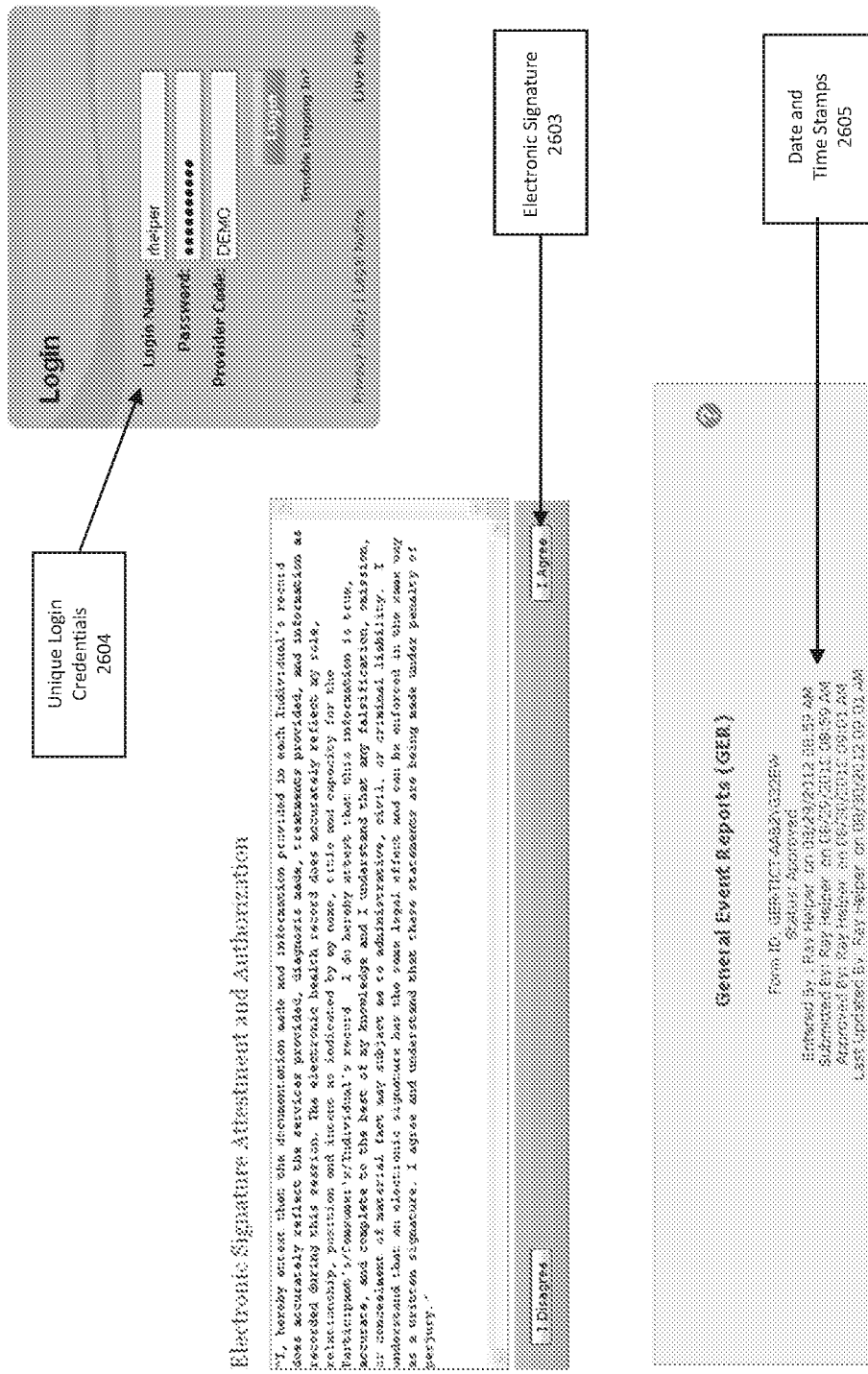
FIG. 26 illustrates a login and electronic signature screen view that may be employed by embodiments of the system and method of the present invention.

A human controlled device refers to the device that a person is holding. For example if a staff member is taking a video of an individual and is connected to the system, the video camera is a human controlled device. There are a number of reasons to separate human controlled devices from an unmanned device. While in both instances the devices could be directly connected to the system over the internet or other method, in a human controlled device the human could have the ability to have an independent ability to login or set instructions, as illustrated in FIG. 26. Also the human has the ability to stop the streaming by moving the camera or taking other actions. A human could also make a real time decision to save data. A human might not have the ability to delete data. But the human may stop filming or capturing data.

In some embodiments, the Person with a device and the human controlled device receives a code to access system either system from a provider administration or through the access rights that the person with deice has. In addition, the person with Device logs in to the system directly from the device to be transferring data The device is not being processing PHI and the process allows data to be transferred directly to the system. Data is all treated as PHI/Protected Health Information or other secure information. The system has the ability to capture data directly without any downloading or capturing on the unmanned device.

The device initially connects to the system for first processing. The system determines if it is an acceptable device to accept data for. It checks for an access code. If the device does not have a password or access rights the system rejects any data which the device tries to send.

If the device is entitled to send data, the system has received an initial setup through the provider administrator to the system which has given information about location, access rights, the device, etc. The system takes this data and knows whether to initially start out transmitting data directly to save/storage or to put in a buffer. Examples of when something might initially go directly to be saved include when a preset location always requiring storage and when a new type of device is desired to be monitored. In addition, there may be instances where the initial setting is not to go directly to storage, but after the system analyzes (135) data, the system sends instructions to automatically save a certain amount of future data without first analyzing that data. Examples of this are if the system notices there has been a fire, then a preset future set of minutes should automatically be saved without the need for additional analysis and when there is abuse and neglect of a person.

When data is not sent directly to save/storage it is transmitted to a temporary buffer (110). The temporary buffer is connected to the physical architecture of the system. There may be a backup temporary storage device. The information is maintained in the temporary buffer until the system analyzes 167 it and decide what actions to take.

The actions and flows to the temporary buffer are tracked and logged 119. However the specific data is not stored at that point. The fact that data came from a certain device may be tracked/logged. But the actual data is still in a temporary buffer.

The data may be associated with caseloads and super-roles and access privileges. At this point the information that the system may have is based on the initial information from the provider administrator and based on location of the device. It is not based on activities which have been analyzed.

The system may then analyze the data. After Analyzing the data there are a few options of what may occur. There may be notifications made 172 and forms filled out. There may be a decision to store data. Storing data gets to the same place as except it is done after an analysis rather than from a preset instruction. Once the data is stored in 121 it is accessed by caseload, role, super-role. This means that the person who first created the data, took the picture, had the device, had a super-role may or may not be able to have access to the data. This is an important part of the system—the ability to have data not available to the person who first created the data based on roles or also analysis of what occurred.

Data is saved in locations which correlate to applications in the system. These may be related to forms, people, locations, roles and other options for future access of the data. The system could decide the access and applications to save the data or an individual could have rights to set this criteria.

A human may have roles, caseloads and access rights to view data in the system. The individual could have the role to require data to be saved. An individual does not have the right to force a deletion from the temporary buffer without saving.

After there the system analyzes the data, the system determines that based on rules and criteria that the data may be eliminated from the temporary buffer (189). The fact that the system eliminated something from the temporary buffer is tracked and logged, but not the actual data itself.

The system may also determine after analyzing that a certain amount of future data should be immediately sent direct to save/storage. The system transmits this information to where future initial data comes into the system.

For data coming after a user login from a device the data may be treated as general data or Human Decided Individual Specific Data. For data treated as general data, this would go into the system and firewall for first processing in a similar manner to data from an unmanned specific device. The system may check that data may be accepted from the device. The system then determines whether data goes into a buffer or is directly stored and saved.

If the data is treated as Human Decided Individual Specific Data the human needs to have caseload and role based access to a list of names for people to submit data on. There are government and security situations where access to a list of names may be restricted. If the human does not have access to a specific name to choose to enter data on, the data may be treated as general data and the system could analyze what occurred, to whom and what actions to take. There may also be the ability for a human to enter the name he thinks is associated with the person in the data. The system may then confirm this name by additional analysis. It is possible in this situation that the person entering this name and data does not have access to this information as if they did not have access to the name they may not have access to the details about a person. These access roles may change in the future if a provider administrator with proper access chooses to change access to an individual to see this information.

The human may enter a request for the system to save all data. The system may be set up so a human might not have the ability to enter a request to delete temporary data that could require an analysis by the system 135. If the human did not request to save all data that may place the data in temporary storage.

Figure 9:
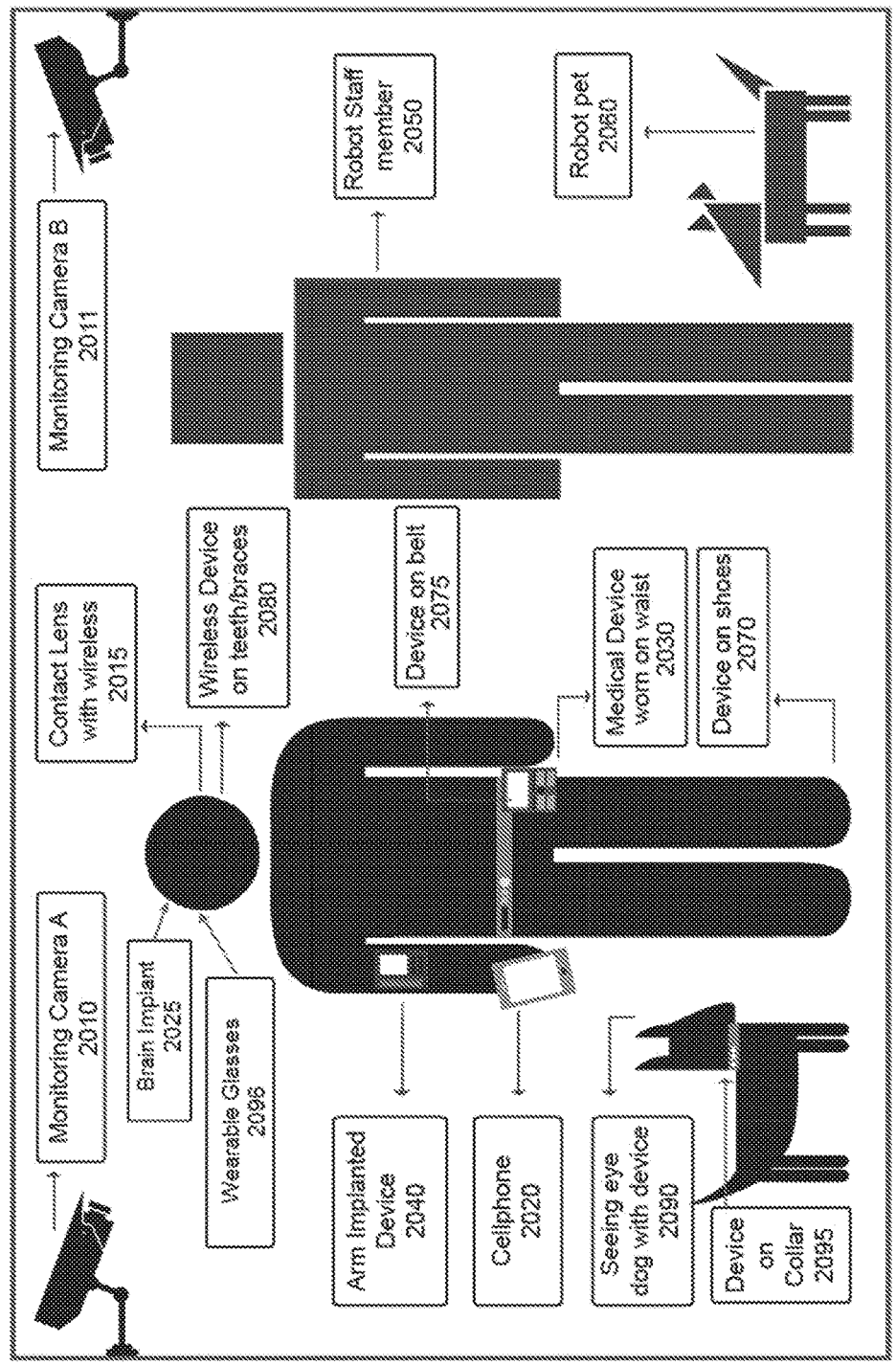
FIG. 9 illustrates ways that embodiments of the system and method of the present invention of may collect data from an individual with disabilities.
Figure 10:
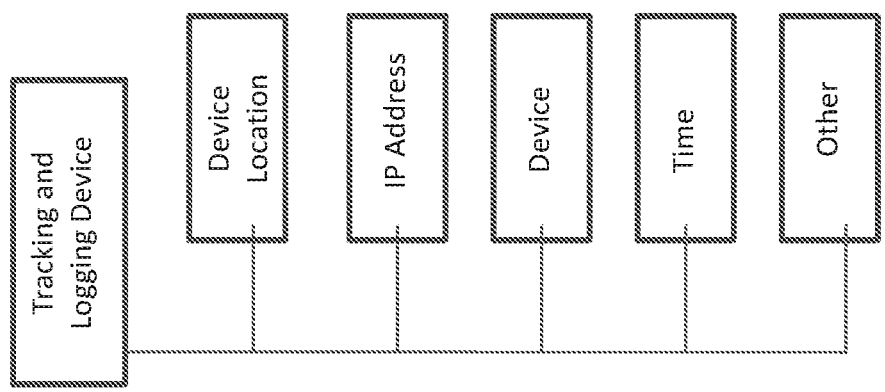
FIG. 10 illustrates a tracking and logging device that may be used in the system and method of the present invention.

FIG. 9 illustrates ways of collecting data from an Individual with disabilities. Data may be collected from wireless devices carried or worn by the individual. There may be cellphones 2020 carried by the individual which records information regarding who contacted the individual, voice tone of the individual while communicating with different people over the phone, information on what was being said to the individual and the reaction of the individual to statements that may be collected and transmitted to the system. Medical devices may be worn on waist 2030, devices on shoes 2070 and belt 2075 which details information regarding the movement of the individual.

Information may be collected from Individuals directly by implanting various devices within an Individual or from the devices in the surrounding of the Individual, all of which transmits information wirelessly to the system. There may be small chips implanted in the brain 2025 which collect information from the neurological responses which are messages receiving "information" from various body tissues via the sensory nerves, or those initiating the function of other tissues such as organs, muscles, etc. Information may also be recorded in the contact lens 2015 and wearable glasses 2096 which enables the system to analyze the data in the surrounding of the individual. There may be multiple monitoring cameras in the room 2010, 2011 to capture information from different angles. There may be arm implanted device 2040 which provides information as the Individual prompts to start recording video. This information, be it high-resolution video or low-quality images supported with sound, will be carried over the Internet or a secure network 108 for Authentication 113.

There may be other devices in the surroundings of the Individual such as Robot Staff member 2050, Robot Pet 2060 and Seeing eye dog 2090 with device on the collar 2095 that may continuously capture data on the movement, facial expression and activities performed by the individual and feed the information into the system.

The system may take information or data straight from the device without saving or storing any information on the device. Data may have a link to bandwidth, internet, access interface or other method of having data reach the Temporary Buffer 164 or immediately saved in the system 125 without having been saved or stored on an interim device.

The activities recorded for video may include walking, turning around, facial movements, eye movements, running, raising of an arm, and eating. Other activities might include counting numbers, pronouncing names, vocalizations, breath sounds and answering to questions. There are a number of reasons this might be of interest. These could include the desire to prove to a government organization entity proof of service delivery, the desire to prove that abuse or neglect may or may not have occurred, the desire to show that an individual met his daily goals or objectives, the desire to learn from a history of actual events to better create a personalized plan for individuals, the desire to prove that staff members may or may not be accurately doing their job including perhaps the ability that a staff member is innocent or guilty of charges, and other objectives. Having a video representation of events which occurred and which may not be manipulated or edited or otherwise tampered or adjusted by a staff member, agency or individual could help achieve the goal of have a record of proof.

Alternative Input Sources 107 may start collecting data with the help of audio, picture, text, monitoring camera, biometrics, brainwave detection, braille, tactile and sensory devices, and other sources.

Figure 5:
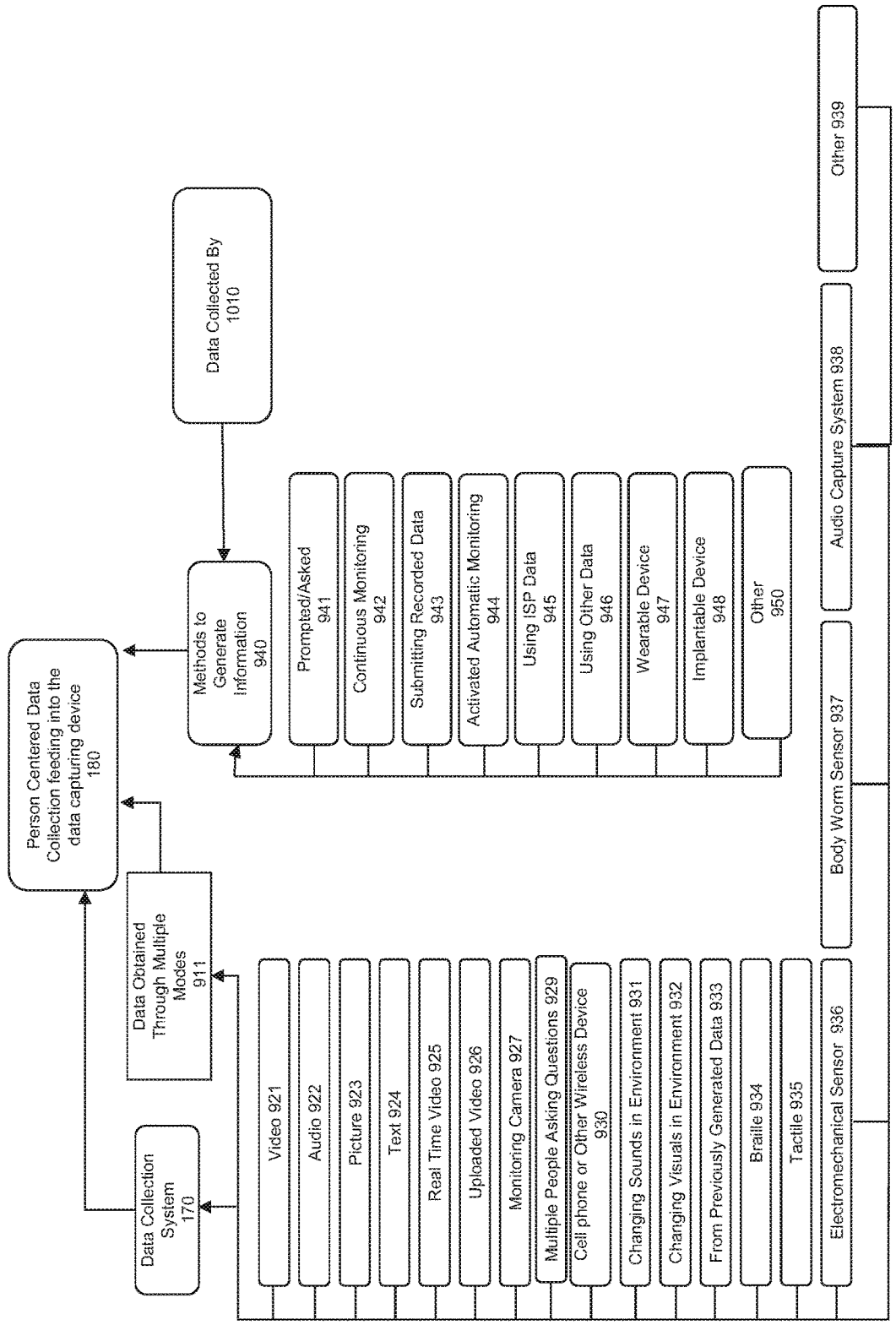
FIG. 5 illustrates how embodiments of the system and method of the present invention collect information by asking questions or gathering information using a wide variety of modes.
Figure 6:
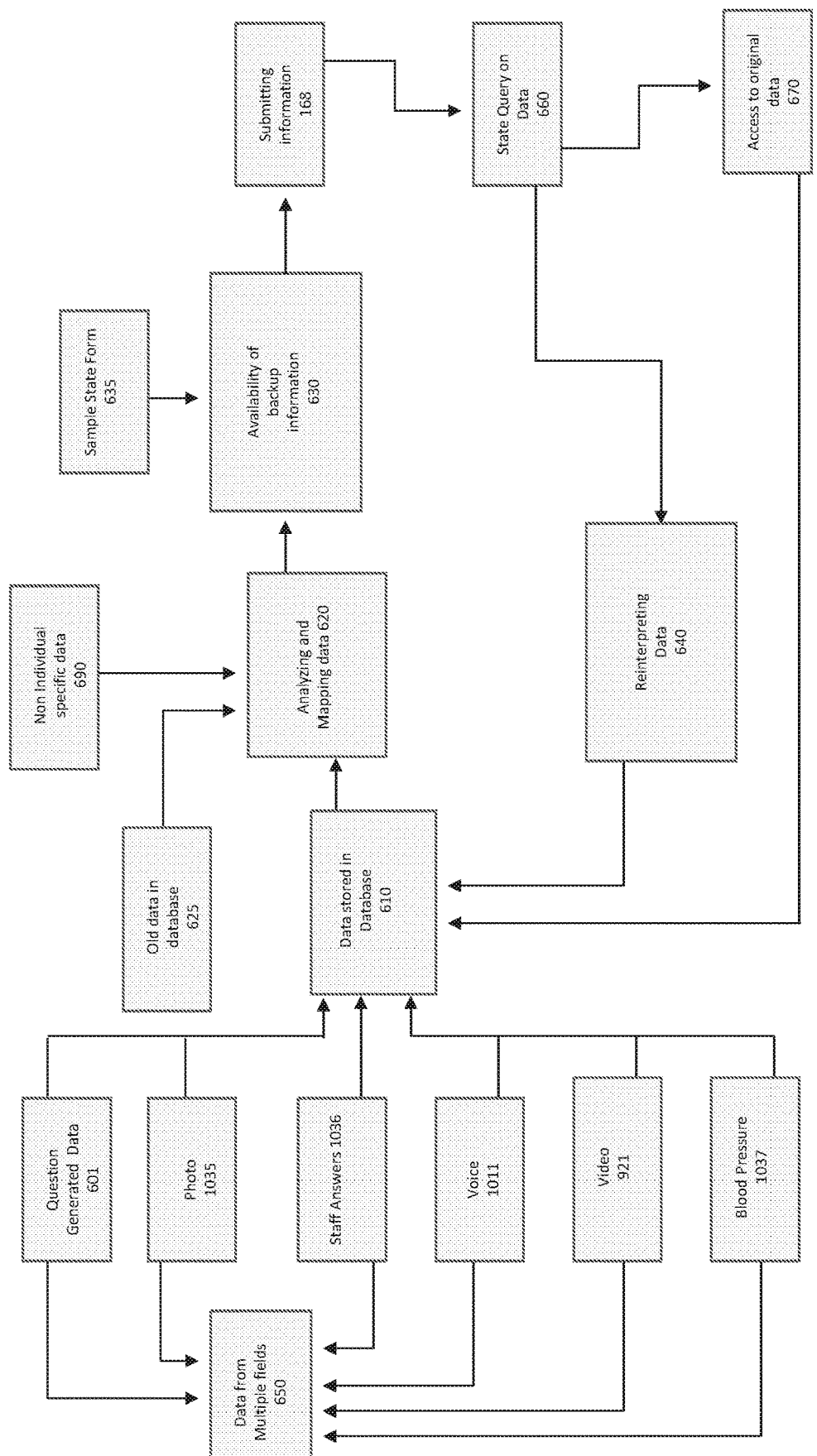
FIG. 6 illustrates how embodiments of the system and method of the present invention may obtain data from multiple fields for a single data point.

FIG. 5 illustrates how the system collects information by asking questions or gathering information using a wide variety of modes. The Data Collection System 170 determines the methods to be used to generate queries using multiple modes. The Data Obtained through Multiple Modes 911 determines the methods to be used to obtain information from multiple modes of the queries. The queries may be generated in different manners depending on who the individual is with, where the individual is and what the current cognitive state at the time of data collection 912. The system may obtain data from multiple fields for a single data point 650.

Figure 7:
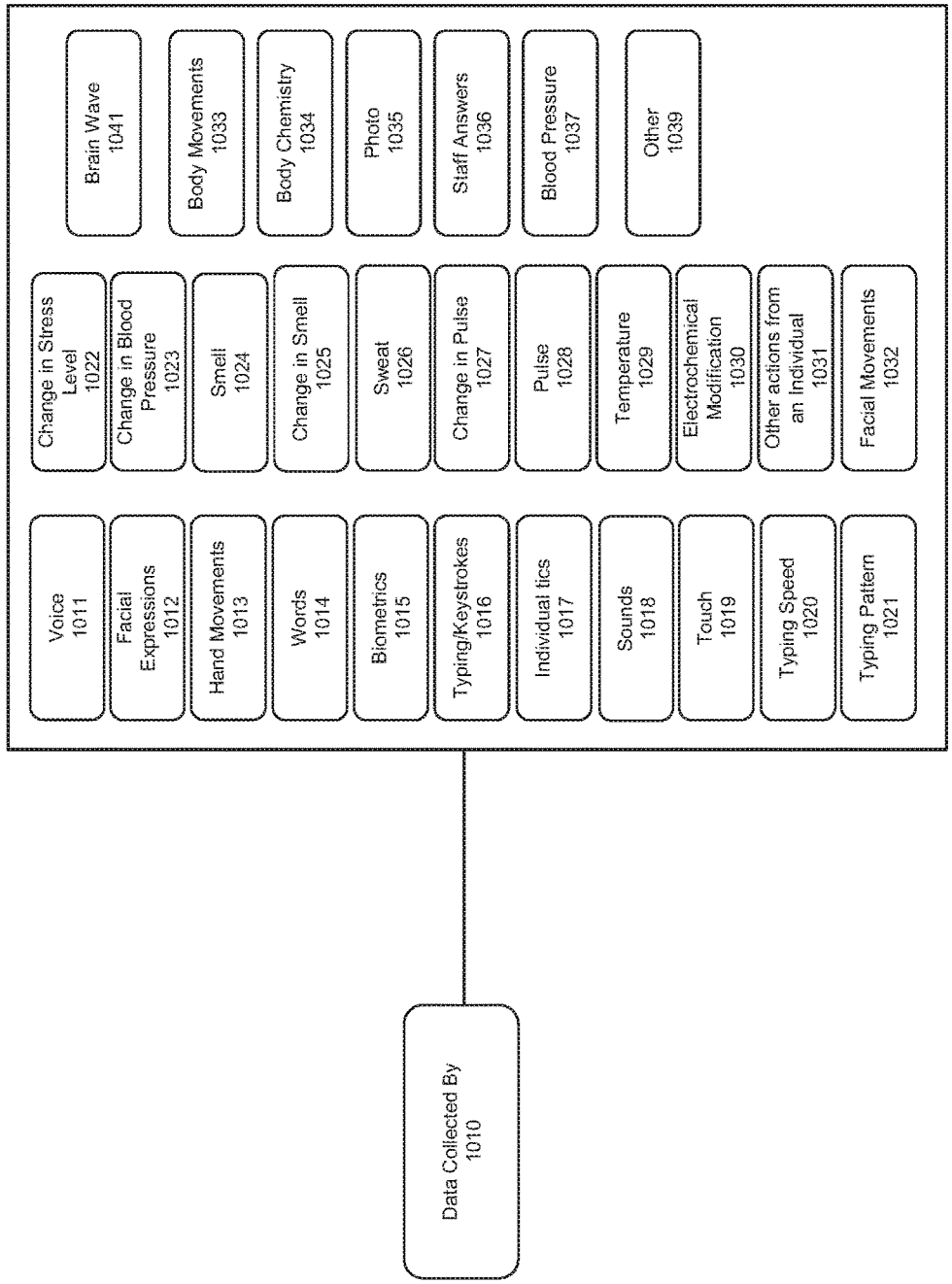
FIG. 7 illustrates how embodiments of the system and method of the present invention may determine individual responses using the information obtained from the individuals or the questions asked to them.

FIG. 7 shows how the system may determine individual responses using the information obtained from the individuals or the questions asked to them. The system may generate queries in multiple modes or may obtain information directly from the individuals in multiple ways as described in FIG. 5. The individuals may respond to the questions or provide data in various modes 1010. These include Voice 1011, Facial Expressions 1012, Hand Movements 1013, Words 1014, Biometrics 1015, Typing/Keystrokes 1016, Individual Tics 1017, Sounds 1018, Touch 1019, Typing Speed 1020, Typing Pattern 1021, Change in Stress Level 1022, Change in Blood Pressure 1023, Smell 1024, Change in Smell 1025, Sweat 1026, Change in Pulse 1027, Pulse 1028, Temperature 1029, Electrochemical Modification 1030, Other Actions from an Individual 1031, Facial Movements 1032, Body Movements 1033, Body Chemistry 1034, Photo 1035, Staff Answers 1036, and Blood Pressure 1037, and any other mode that is utilized.

Figure 11:
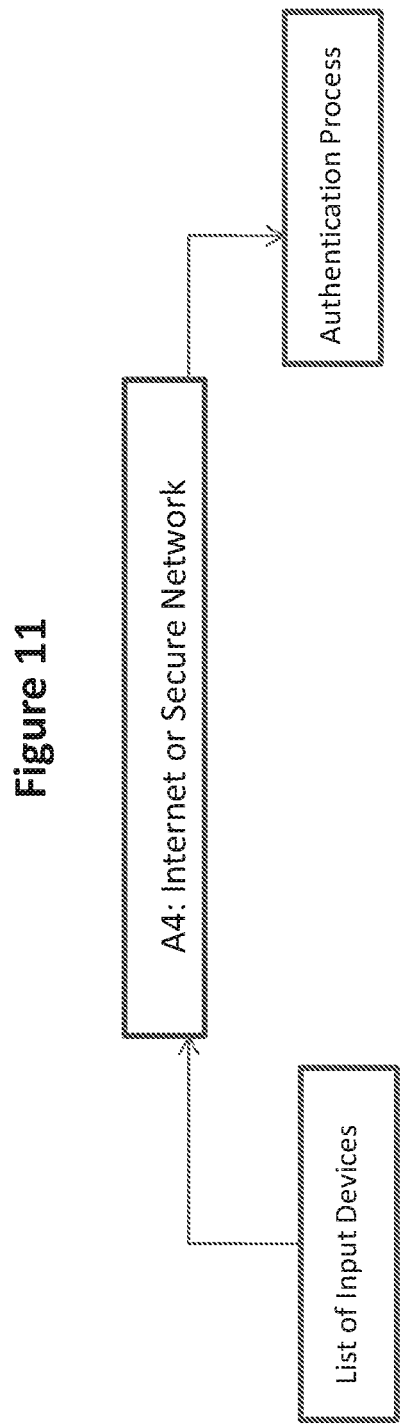
FIG. 11 illustrates information from data capturing devices being transmitted over the internet or secure network for authentication.
Figure 12:
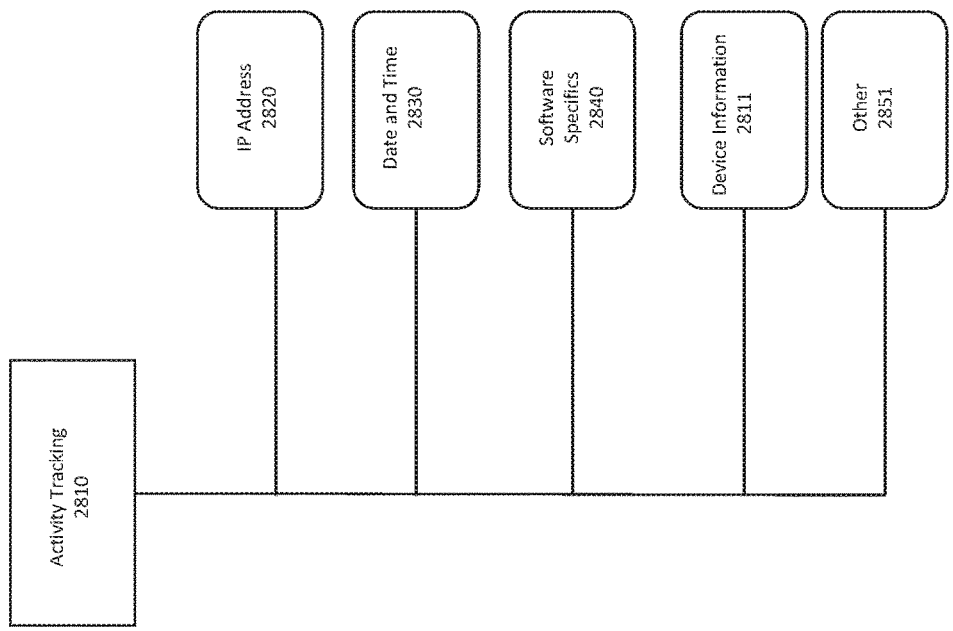
FIG. 12 illustrates activity tracking regarding temporary data.

FIG. 11 illustrates information from data capturing devices being transmitted over the internet or secure network for authentication.

Information from the data capturing devices passes over the Internet or secure network which is then validated by an authentication process. This authentication is checking that the devices are acceptable to send information into the system.

Figure 13:
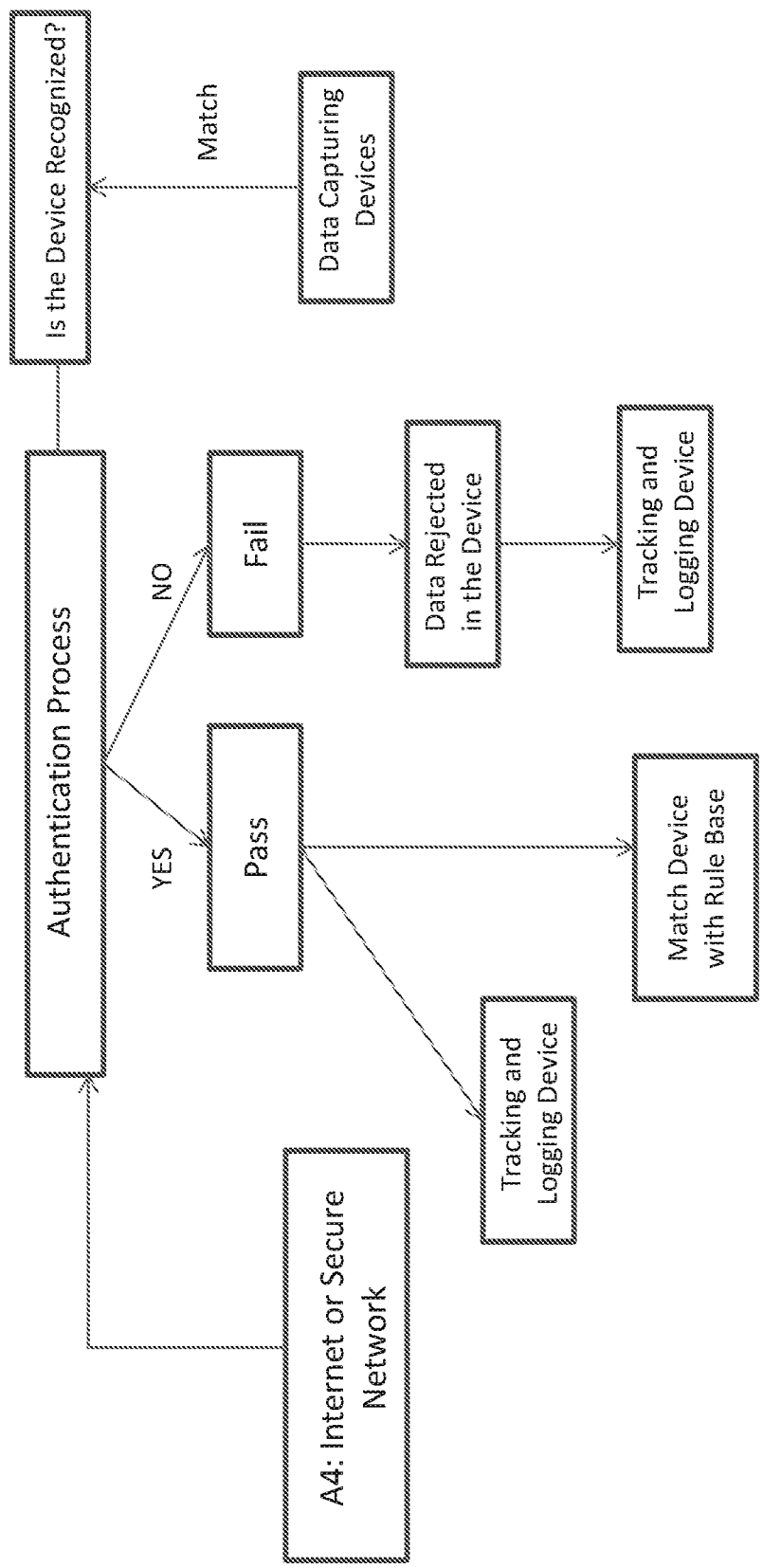
FIG. 13 illustrates the detecting of data capturing devices as part of an authentication process of embodiments of the system and method of the present invention.
Figure 14:
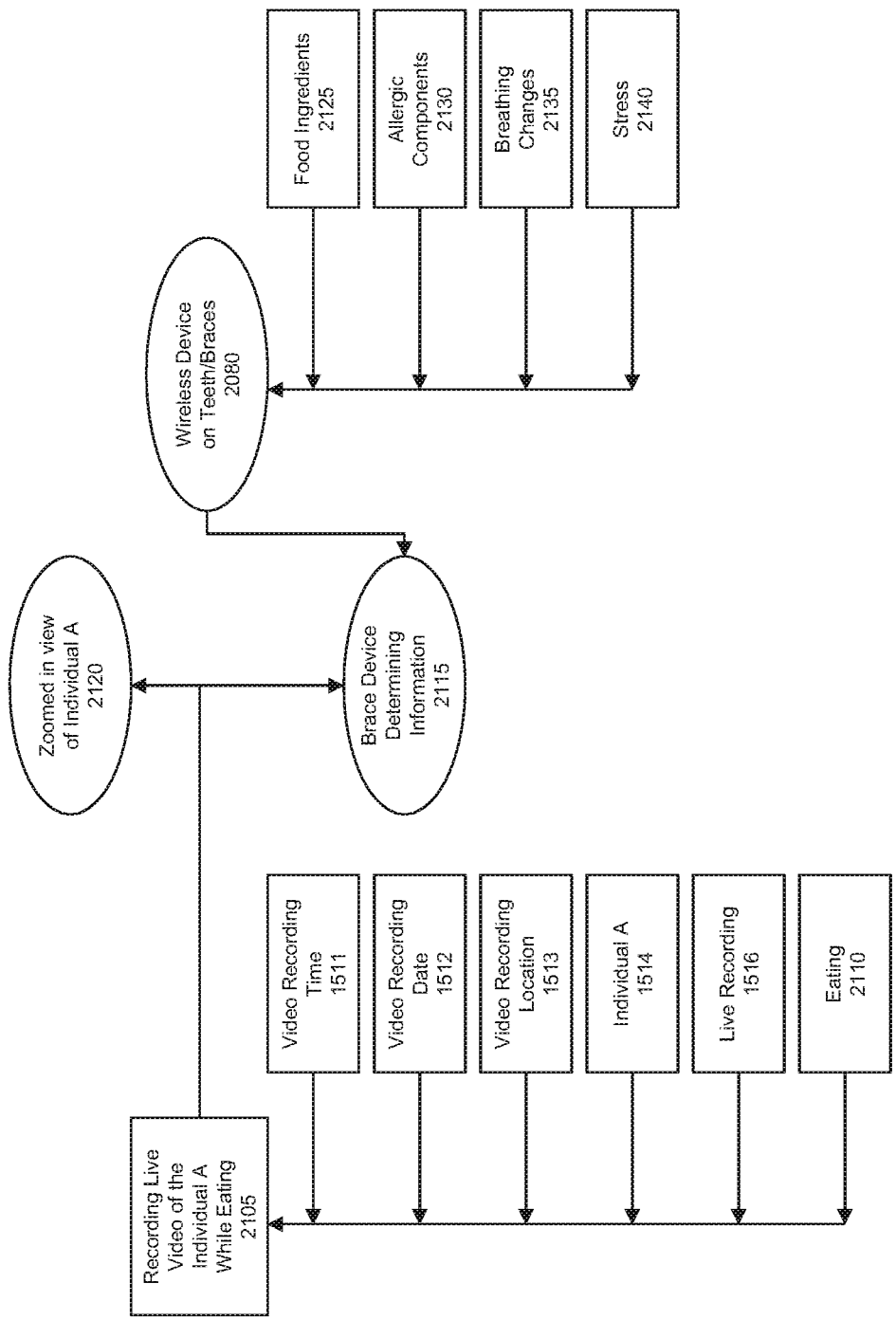
FIG. 14 illustrates an example of device capturing information of embodiments of the system and method of the present invention.

FIG. 13 illustrates that the authentication process goes through the phase of detecting the data capturing devices. At this point the actual data may not be what is being authenticated. So for example the system has to recognize that the devices connected to the internet are eligible to send data to the system. These steps are logged and tracked. So data from a given device which was a fail in the authentication process may still have information which might include time, date, IP address, camera information, quality of video, sensors and other information logged and tracked in the system. The system might not be storing or analyzing what that data was as part of the tracking and logging. Data which was failed would have its data rejected. This information is and other information tracked and logged. These devices then pass through a rule base which is predetermined based on several factors including device location, location, list of incidents previously occurring in the location and other factors. On the basis of the rule base the device will either be stored immediately to the database or kept in the buffer.

Figure 15:
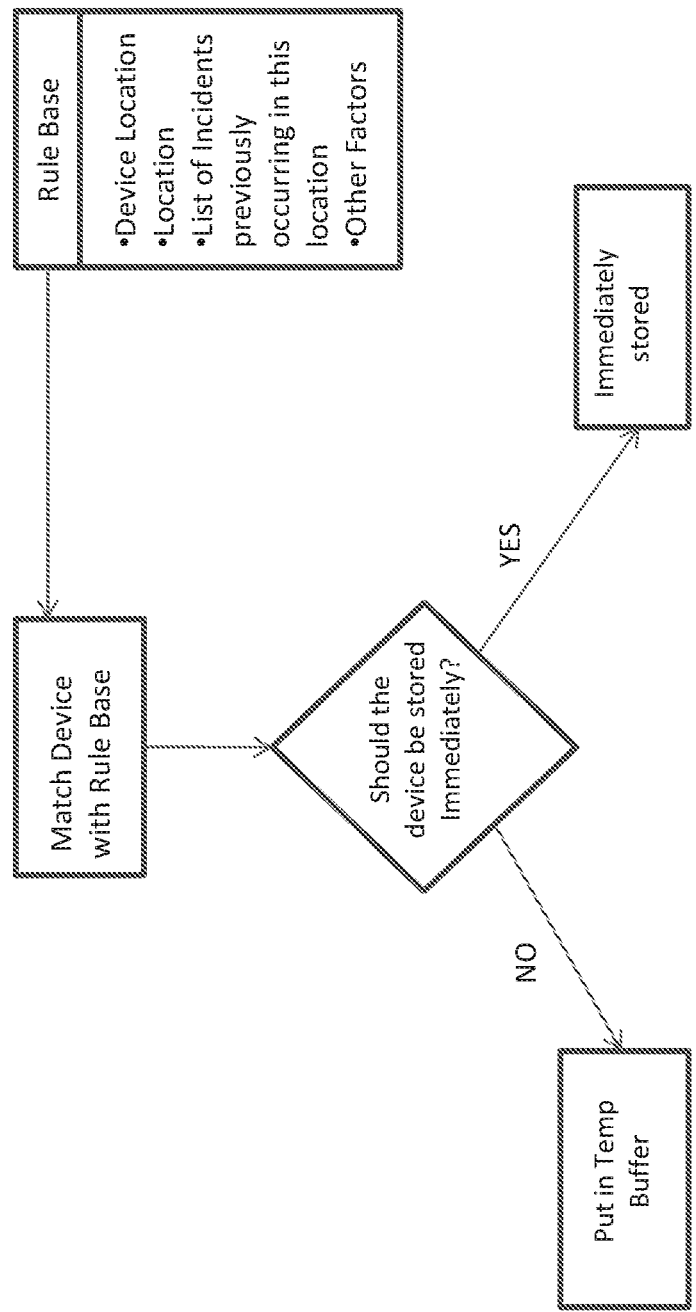
FIG. 15 illustrates how embodiments of the system and method of the present invention match data capturing devices with a predetermined rule base.

FIG. 15 illustrates matching the data capturing devices with the predetermined rule base. The data capturing devices are checked with the rules in the rule base. The system has not yet stored or looked at specific information about the video or other data objects. The system analyzes the rule base given the device. At that point data is either be placed in a Temp Buffer which is a temporary condition which is not saved to a permanent storage solution or is stored immediately. The devices that match with certain rules in the rule base are immediately stored to the database and instructions are generated to store the device information and data from these devices directly into the database for a definite amount of time.

Figure 17:
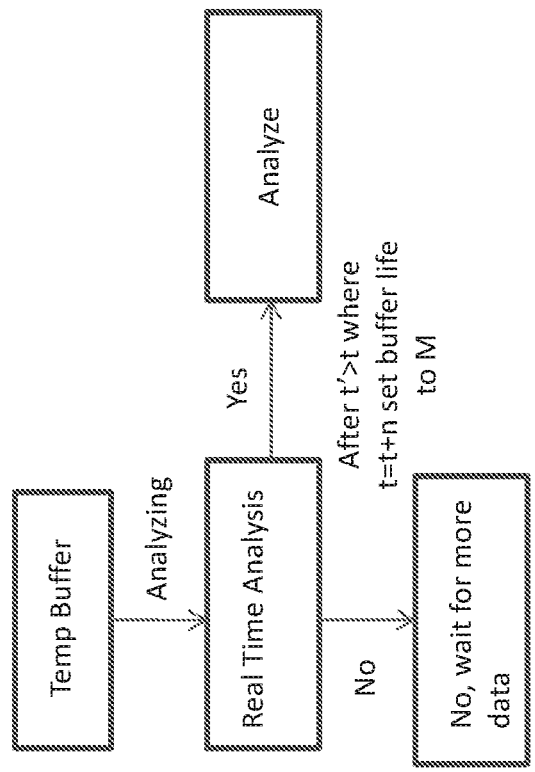
FIG. 17 illustrates how embodiments of the system and method of the present invention perform real time analysis of information kept in a temp buffer after matching with a rule base.
Figure 18:
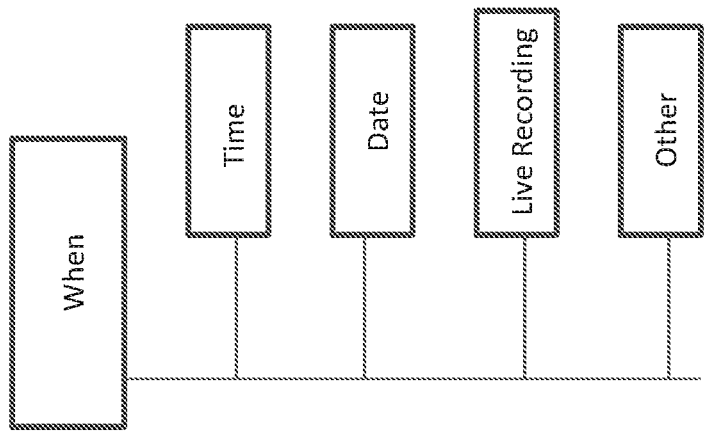
FIG. 18 illustrates aspects of the analysis of when data was recorded.

FIG. 17 illustrates the real time analysis of information kept in the temp buffer after matching with the rule base. The system would look to see if an analysis should be performed. The first time data is received from a specific Person-worn device, Device or Alternative Input Source an analysis occurs on when to do the analysis. For example, if there is a video feed, there is not continuous analysis on the stream of data. There is an initial setting of "N" seconds which may be set by either a rule for the device or by the system default if there is no device rule for when an initial analysis should occur. The time since the last buffer may be greater than the interval for analysis. If not, then the system waits for more data.

Figure 19:
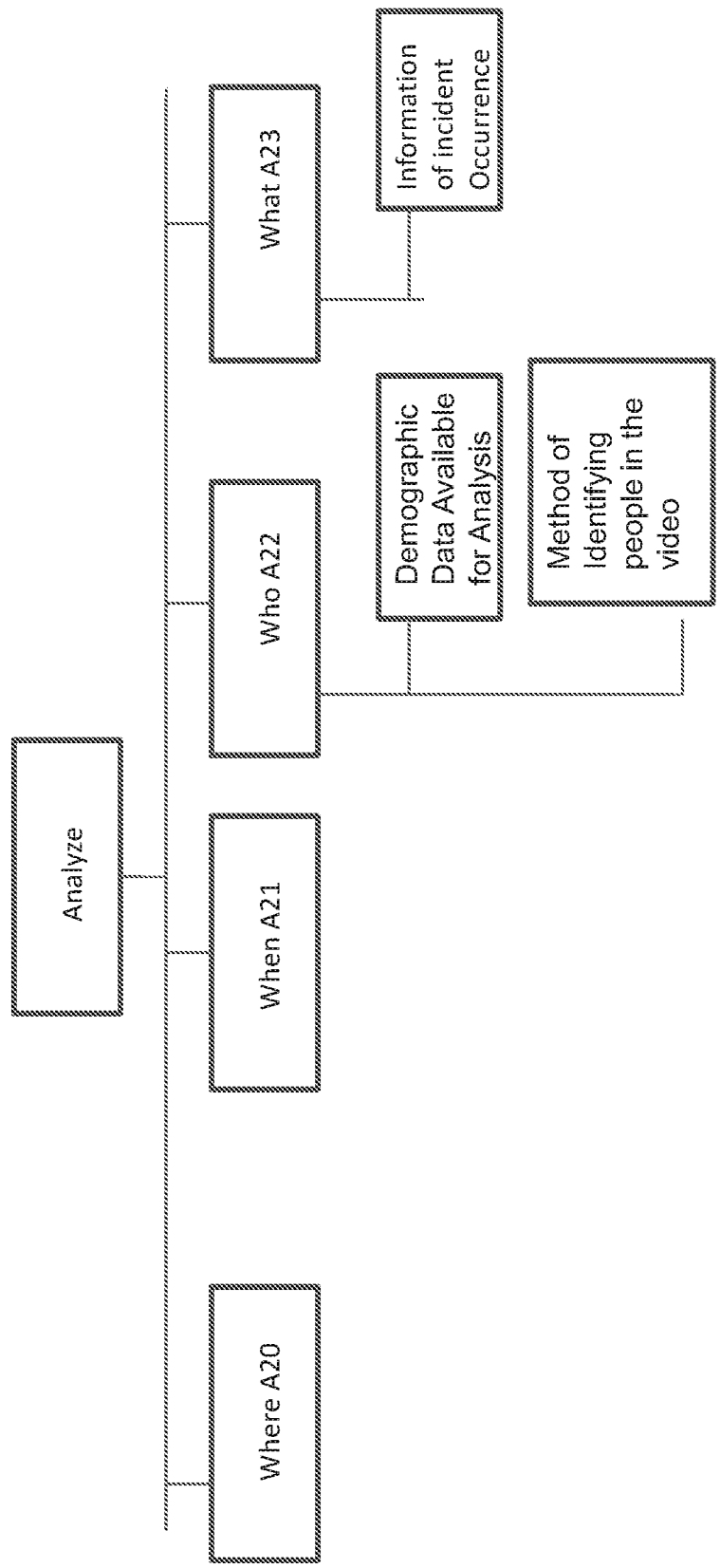
FIG. 19 illustrates the analysis of information captured by data capturing devices of embodiments of the system and method of the present invention.

FIG. 19 illustrates the analysis of information captured by the data capturing devices. The first part of the analysis could be finding out Who (A22), What (A23), When (A21) and Where (A20) regarding the actual data. At this point the system may be looking at the video or audio or sensor data. The system may track and log the analysis it is doing. The system is not storing the actual raw data objects but the type of analysis it was doing and the rules it was looking at. The system may log where the data was from, who was in the video, when the data was created and what occurred.

The system identifies the location from where the information is being collected by devices using technologies such as Video Cameras, GPS, CCTV, and other technologies that help determining the exact location of the device. The information collected by the devices passes through further analysis as determined by documentation, analysis field requirements and other requirements.

The time and date is also recorded by the system which may help in determining when services were provided, keeping track of timely delivery of services and thus complying with state, funding agency and other requirements. The system may also have the technology to ensure that the data being collected is live and in real time by generating voice messages which may be numeric or alphanumeric and allowing individuals to repeat the same messages within a specific time period. Time specific information is crucial for the proof of service delivery and accurate reporting on the achievement of goals, satisfaction of service received, or potential problems such as abuse and neglect.

Another important aspect of the system is to identify the people in the video. The system may identify people in the video using a number of methods which may include voice, biometrics, previous logs, biometrics match, verbal password and others. The location may also help in identifying the people in the video and if the person is unidentifiable the system may guess depending on factors such as location, previous history of individuals, staff present with the individual, knowledge of staff, families and other individuals and other factors. The system may also take human assistance in identifying the individuals in the video, a combination of methods or other methods to identify individuals. The system might always reinterpret information based on information analyzed later and on the basis of other factors and save the accurate information in the database.

Figure 21:
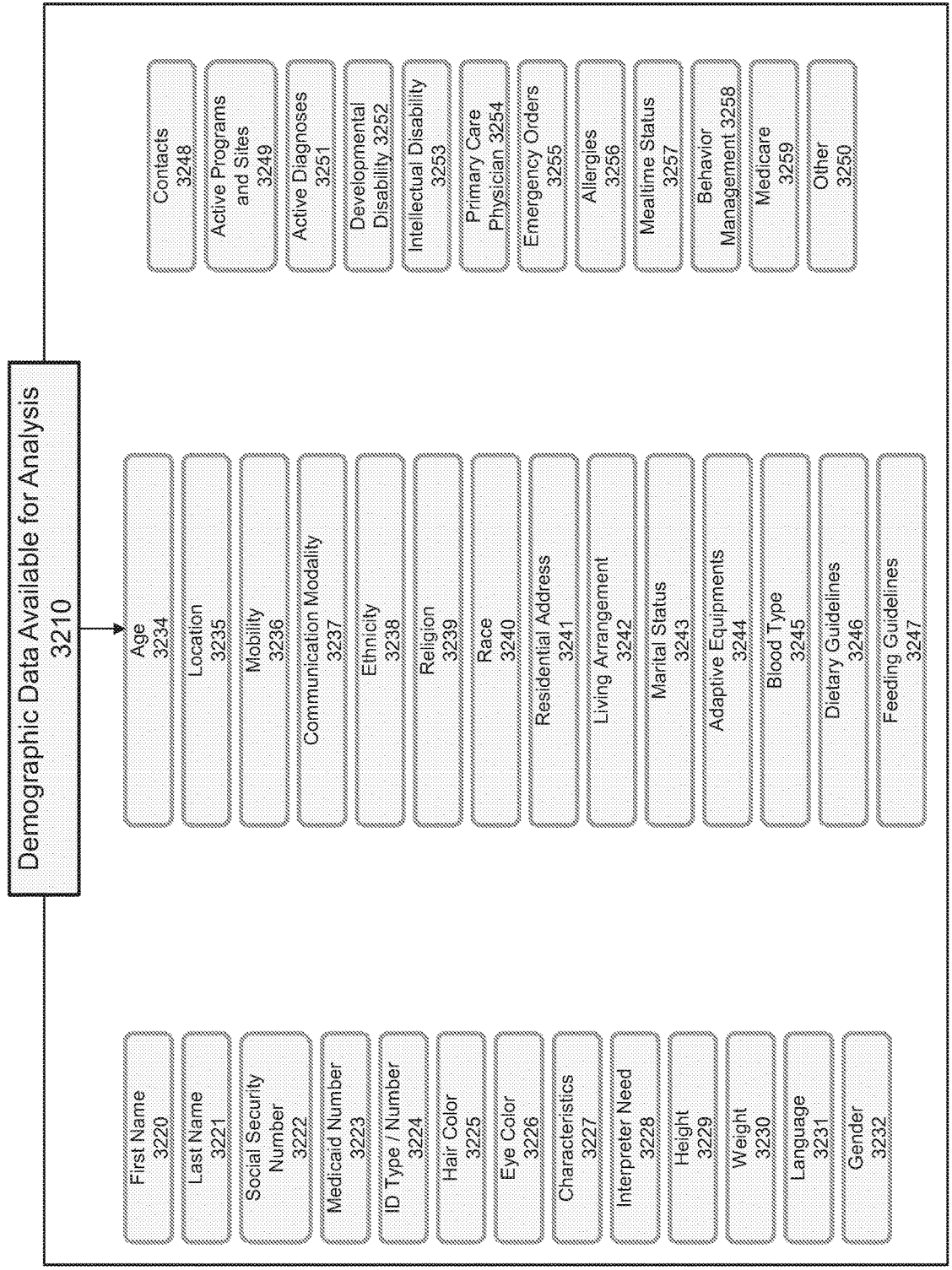
FIG. 21 illustrates demographic data that may be used in embodiments of the system and method of the present invention.
Figure 22:
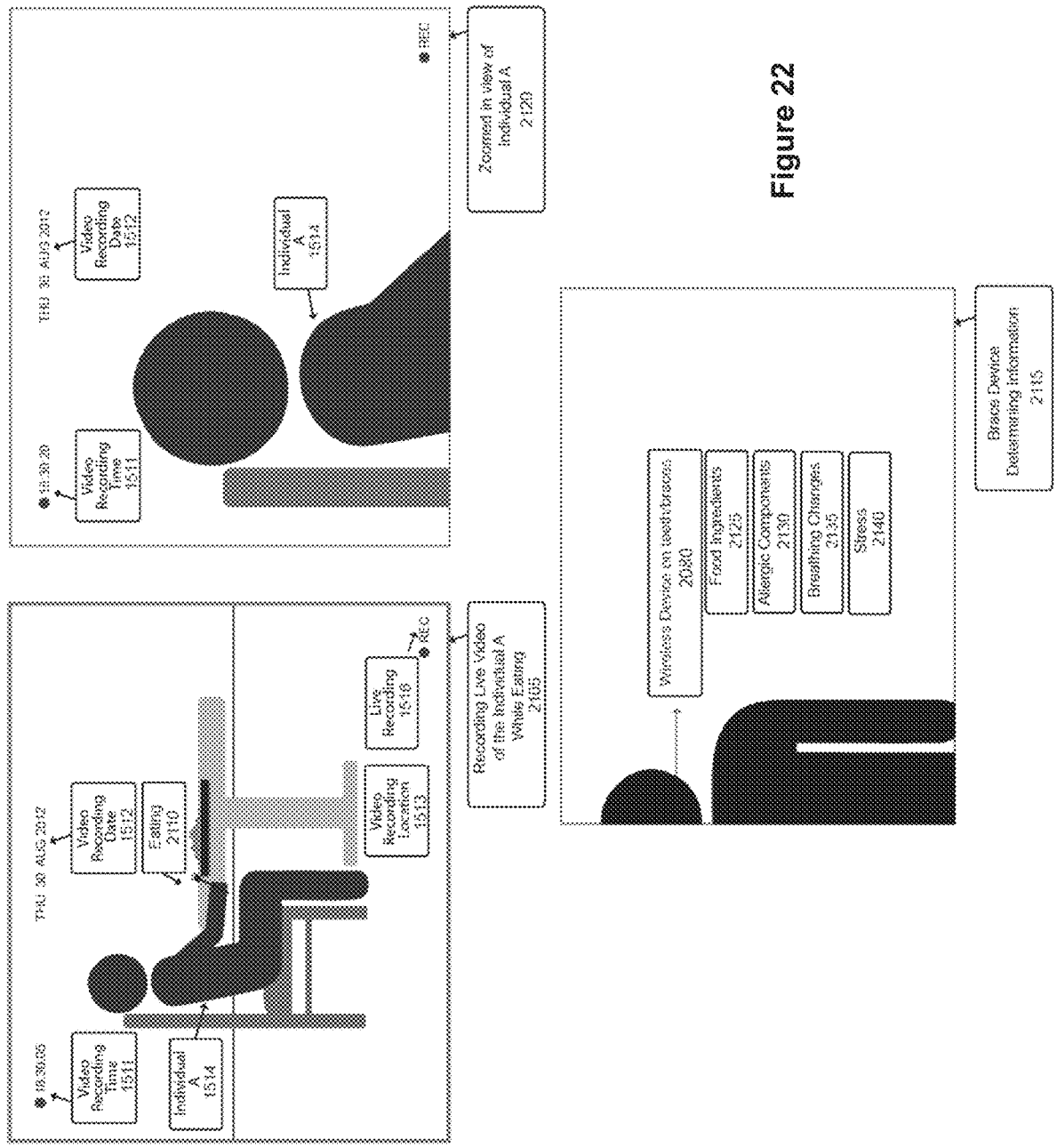
FIG. 22 illustrates an example of an individual in a video recording.
Figure 23:
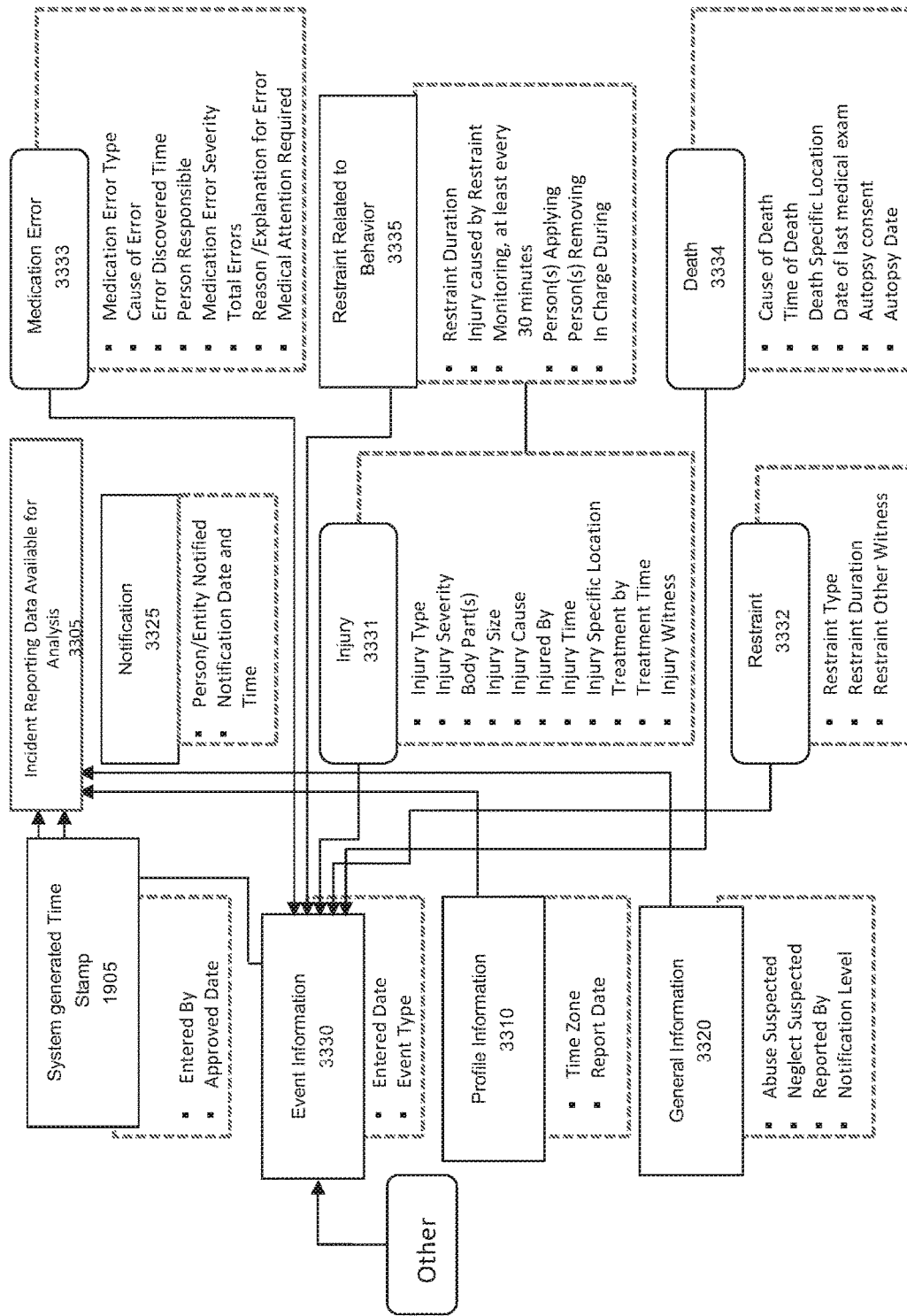
FIG. 23 illustrates event information that may be recorded by embodiments of the system and method of the present invention.

As illustrated in FIG. 21, the system has demographic data of individuals, which may be used by the system for identifying people in the video and performing necessary analysis. This information is also helpful when the system comes to the point of reinterpreting information.

The system identifies what is occurring on the video using the knowledge of the activities occurring in the previous day, previous period activities, library of activities, expected activities from ISP goals for Individuals, individual specific list of activities, individual list of activities from ISP and other tracked goals and agency specific list of activities. The system may also identify locations using the government created list of activities, government created list of abuse or neglect, societal created list of activities and other list of activities. The system may further analyze the data captured to determine the occurrence of the incident if the system has multiple options and may choose to save the data in a higher quality format.

Figure 31:
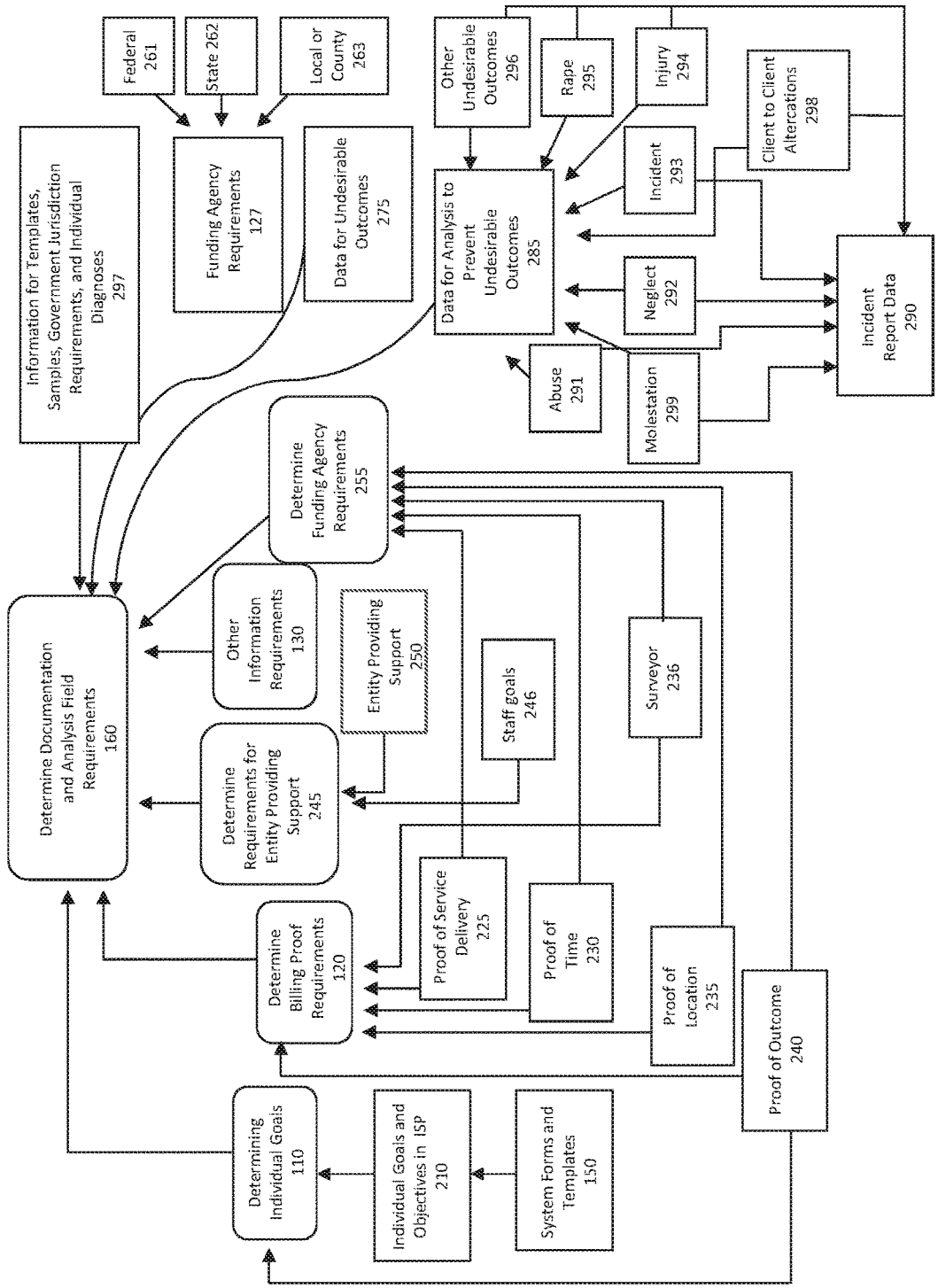
FIG. 31 illustrates how documentation and analysis field requirements may be determined by embodiments of the system and method of the present invention.
Figure 32:
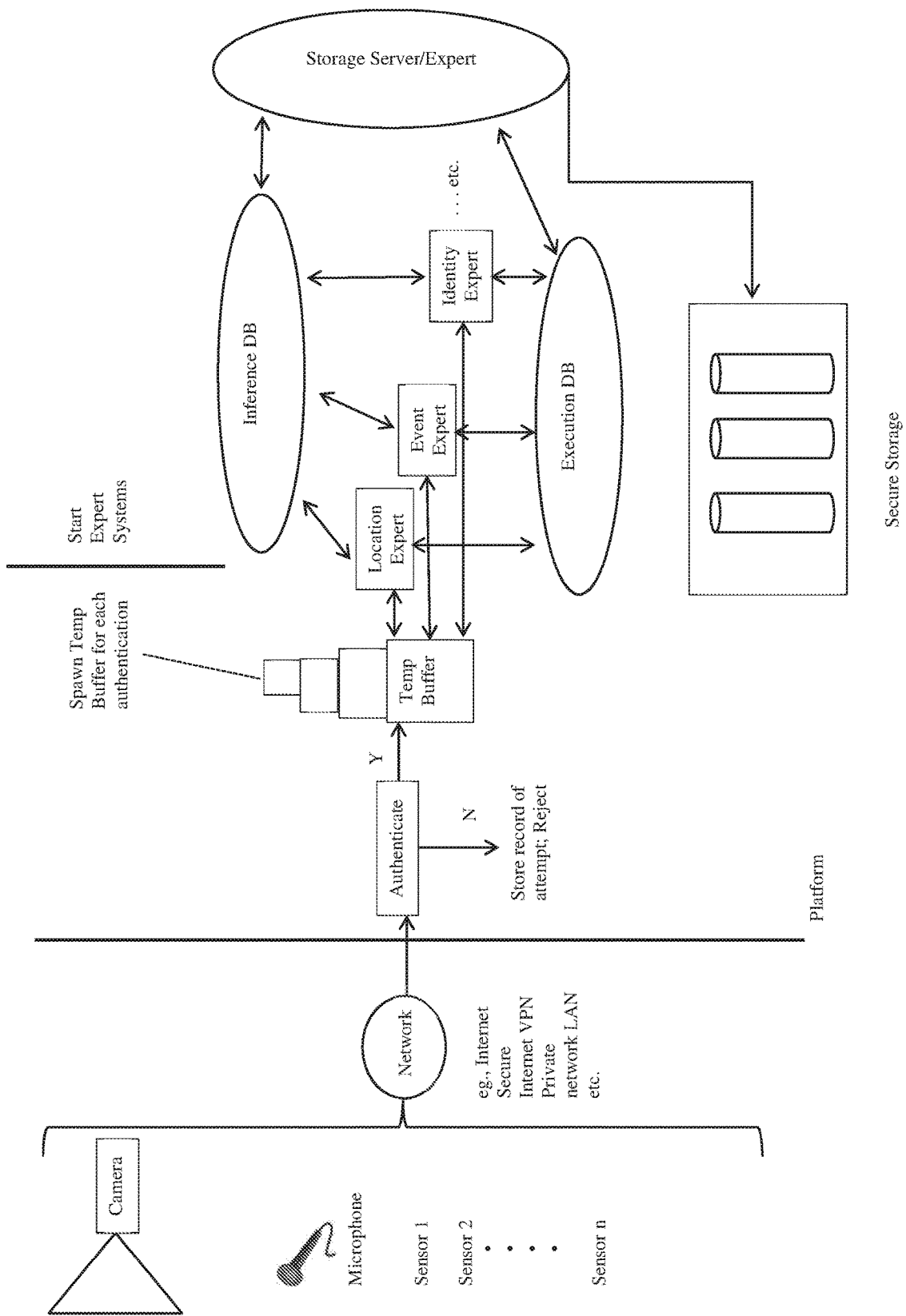
FIG. 32 illustrates an expert system embodiment of the system and method of the present invention.
Figure 33:
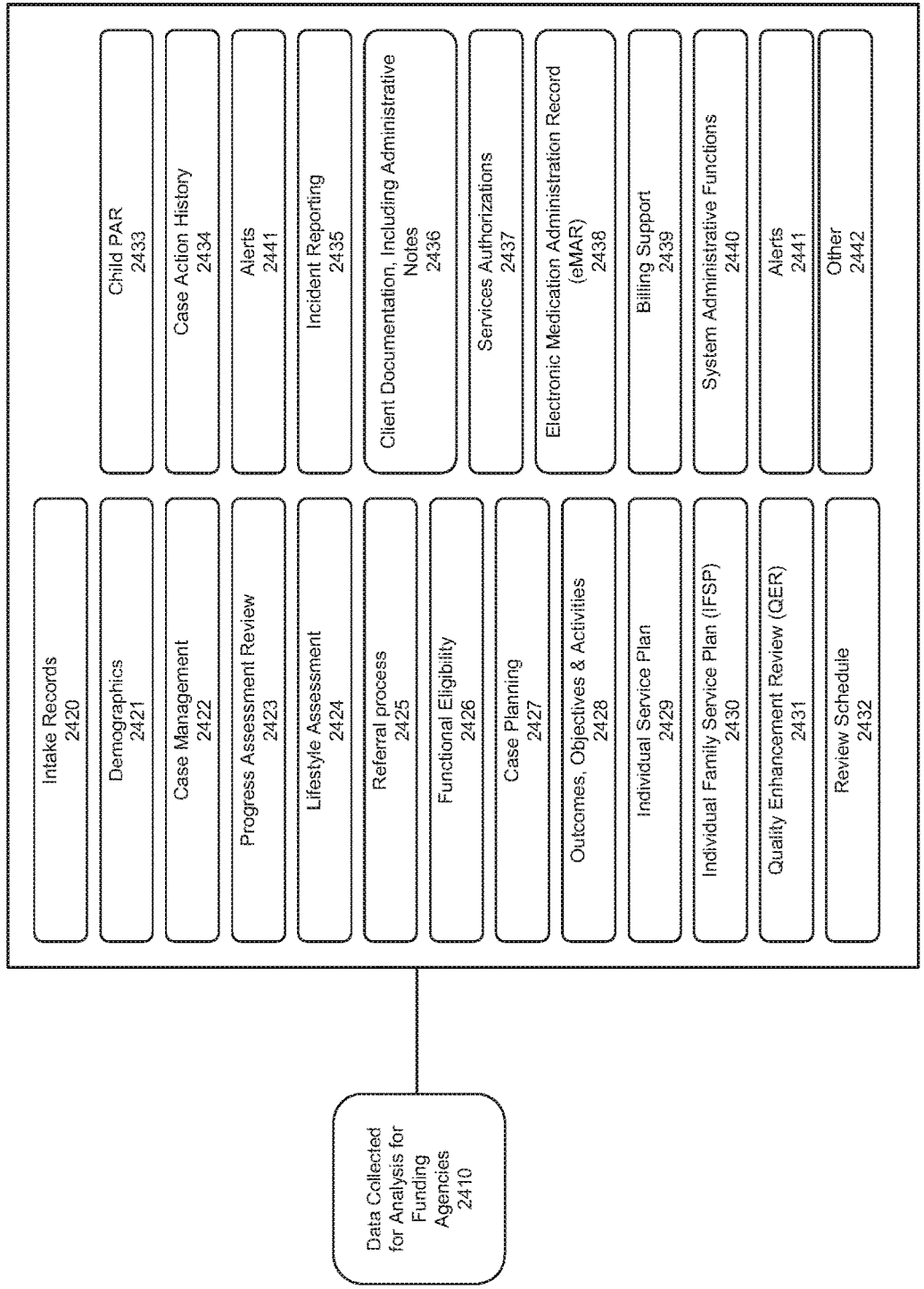
FIG. 33 illustrates data that may be collected for analysis for funding agencies by embodiments of the system and method of the present invention.
Figure 34:
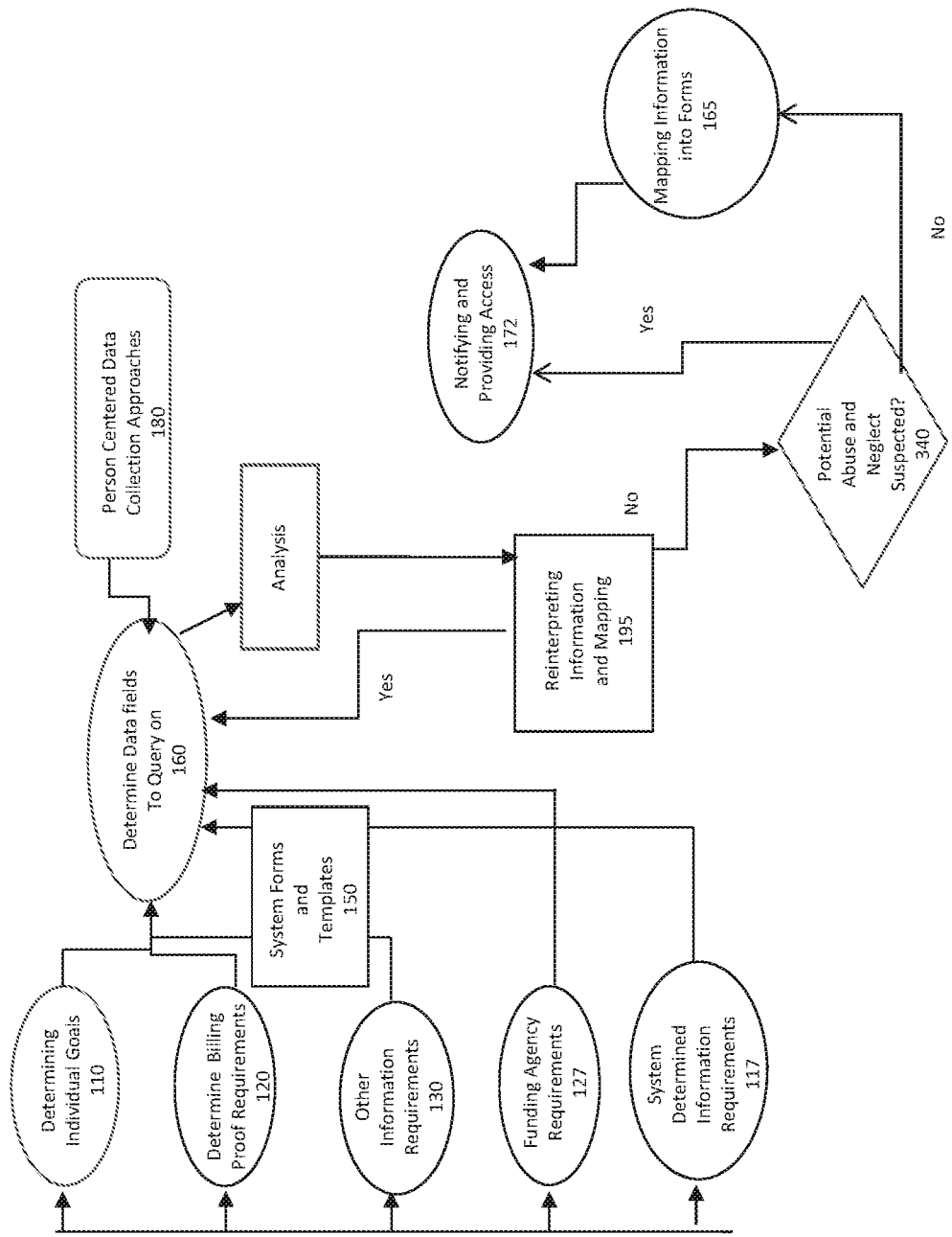
FIG. 34 illustrates methods for notification based on requirement that may be performed by embodiments of the system and method of the present invention.
Figure 35:
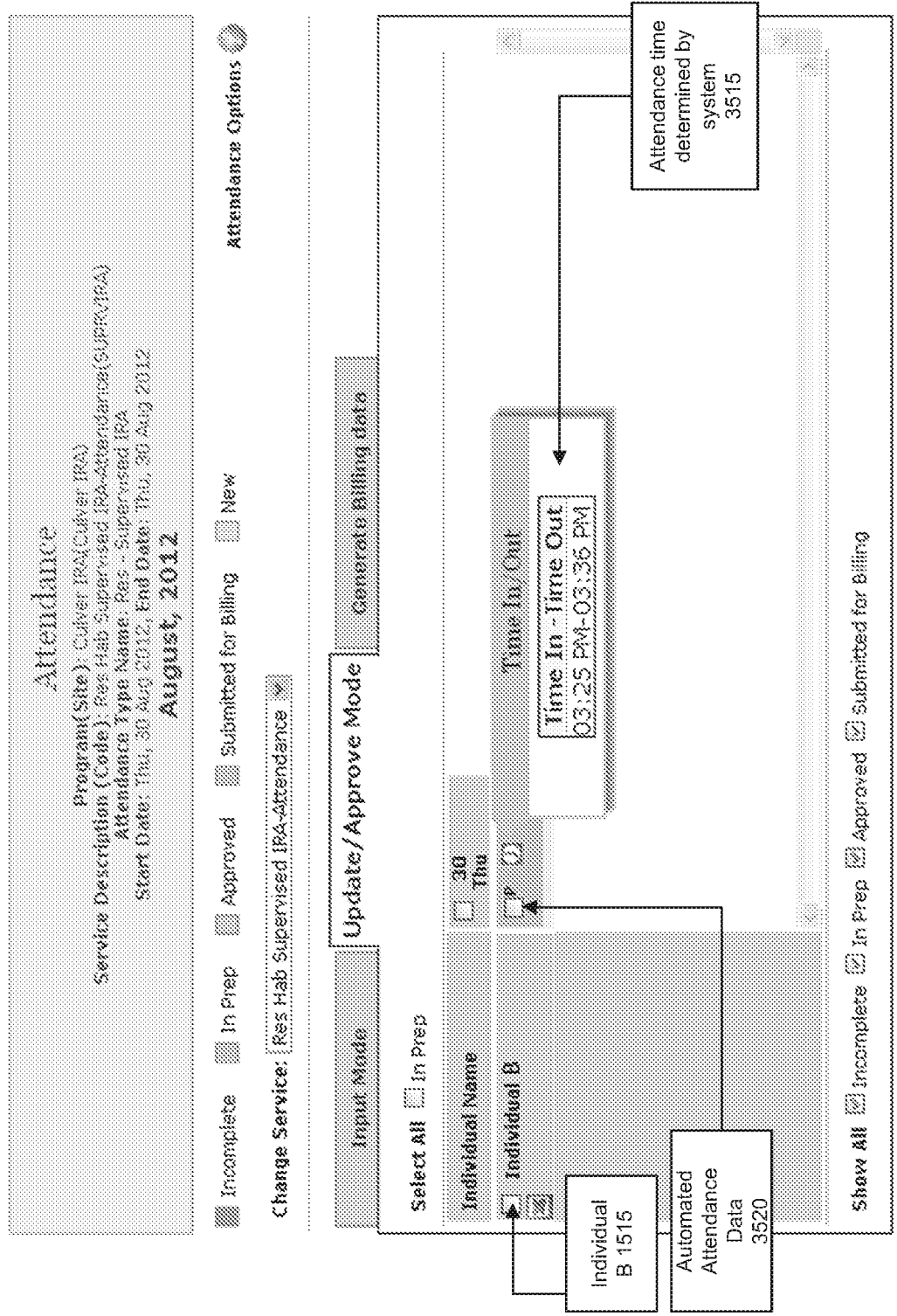
FIG. 35 illustrates an attendance screen view that may be generated by embodiments of the system and method of the present invention.
Figure 36A:
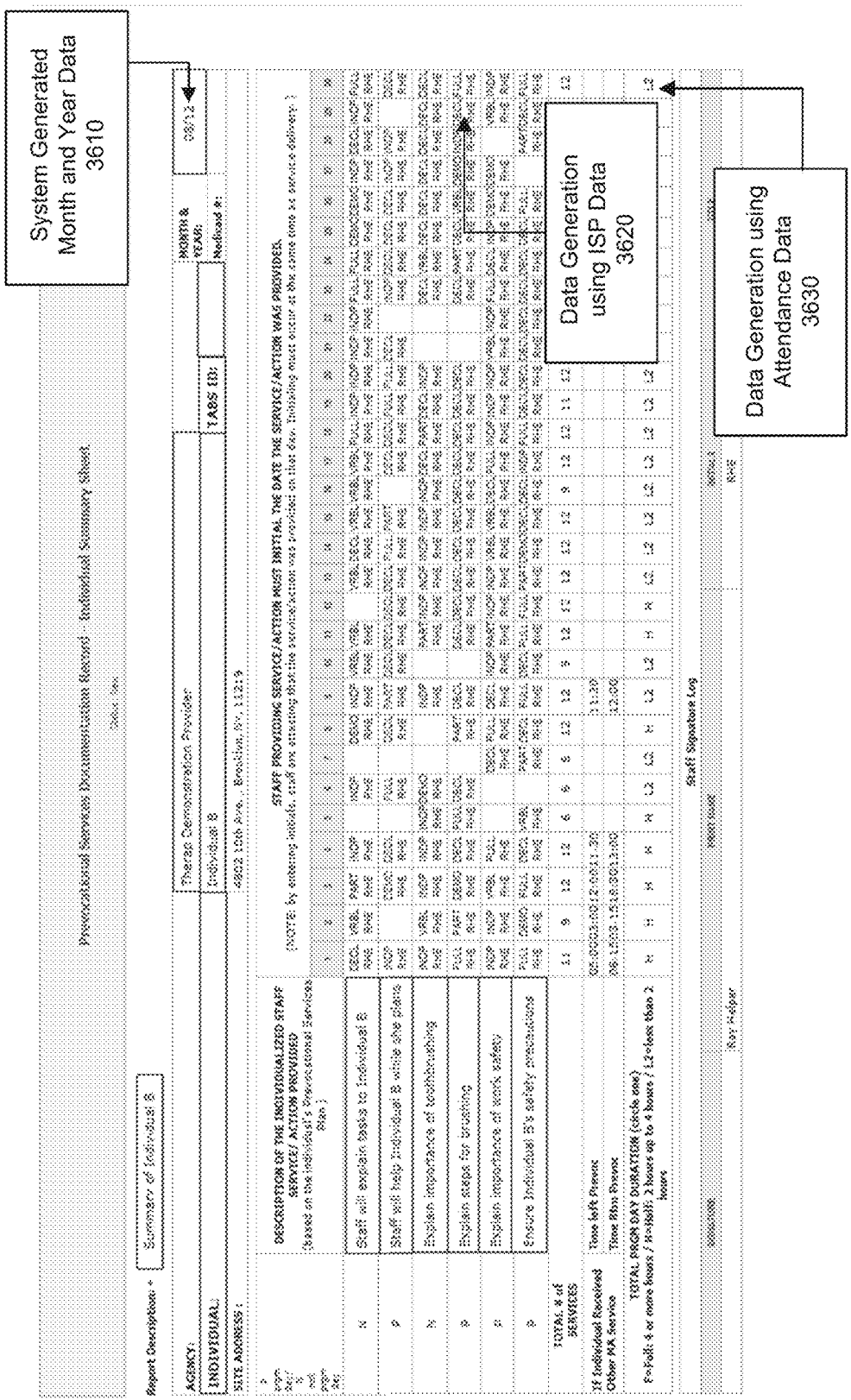
FIG. 36A illustrates a prevocational services documentation record screen view that may be generated by embodiments of the system and method of the present invention.
Figure 37:
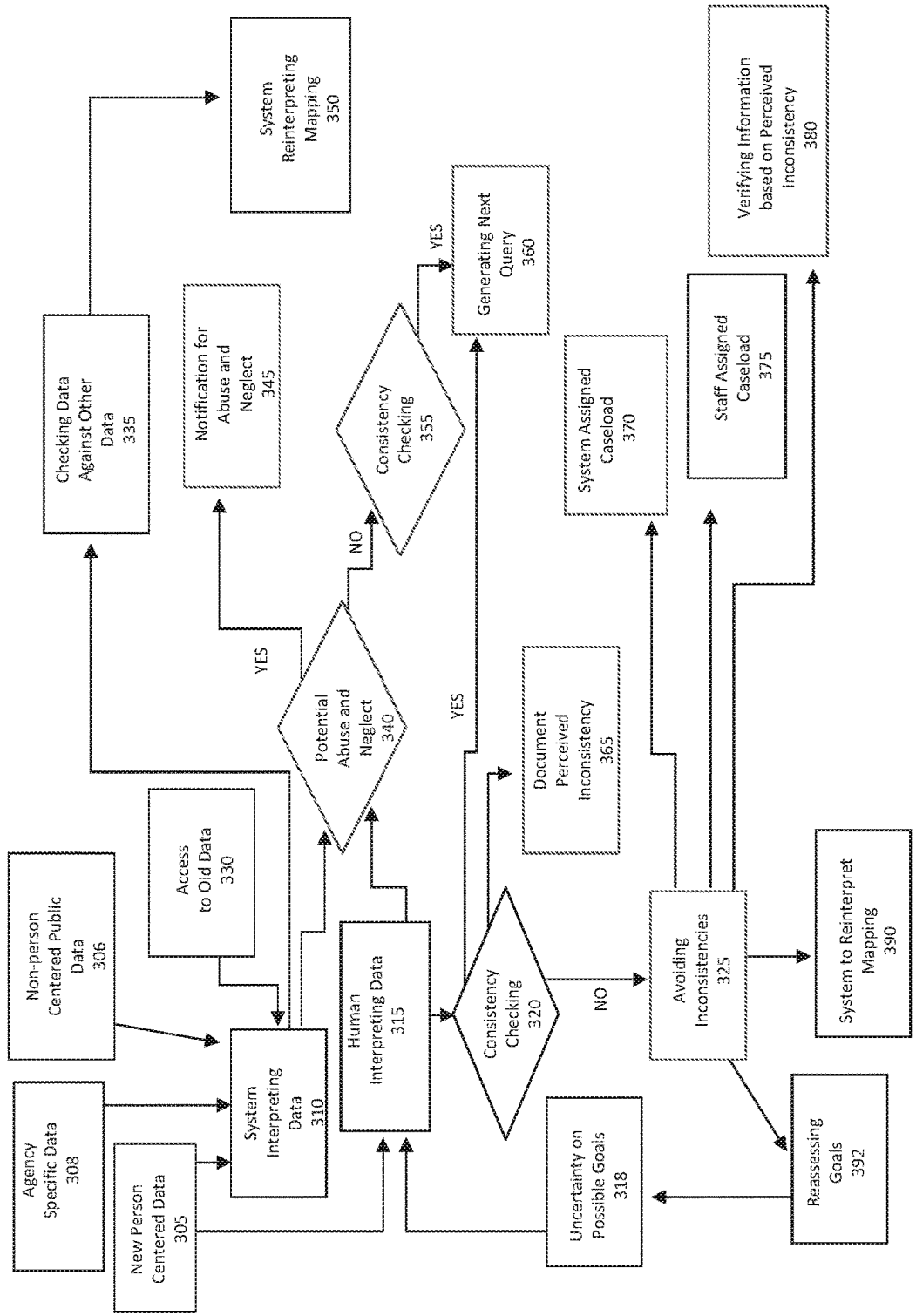
FIG. 37 illustrates a method for determining potential abuse and neglect that may be performed by embodiments of the system and method of the present invention.
Figure 38:
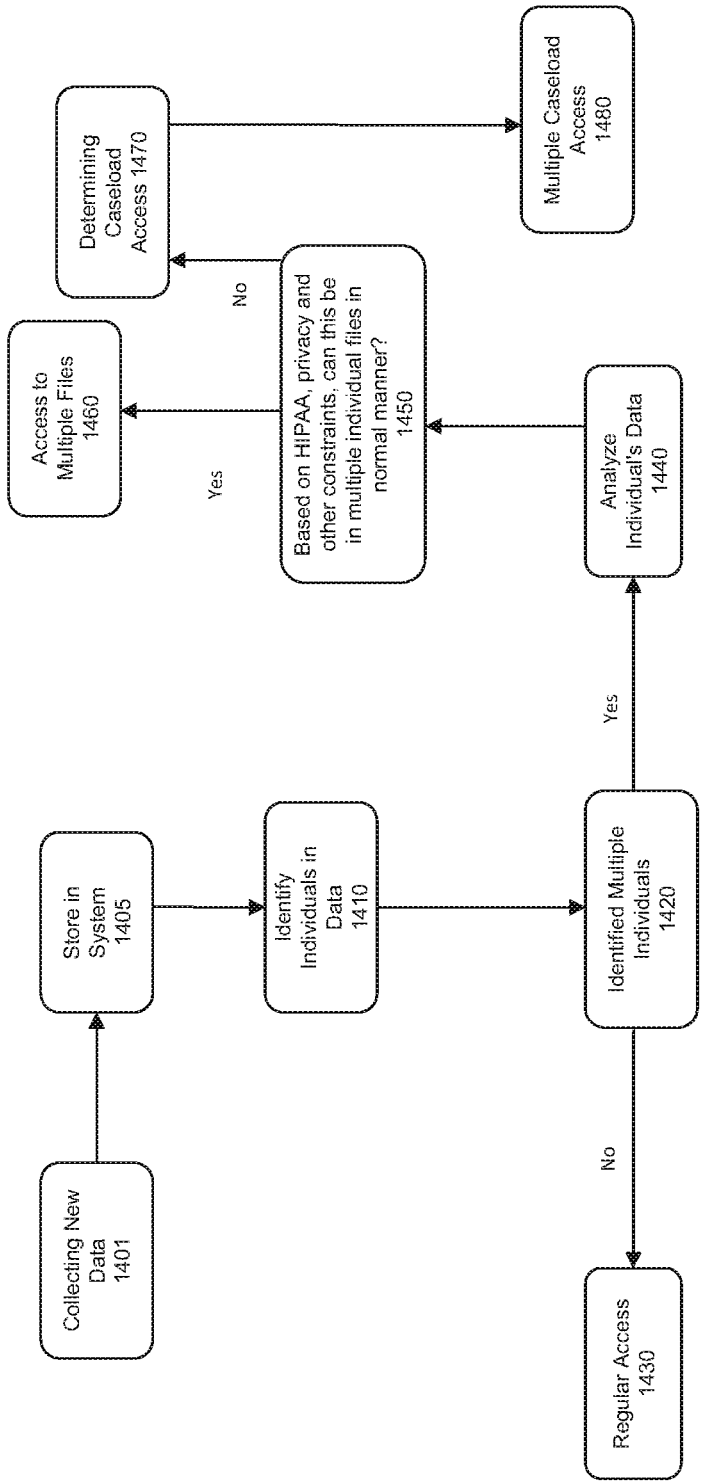
FIG. 38 illustrates a method for determining caseloads for multiple individuals that may be performed by embodiments of the system and method of the present invention.

After the system determines as much as possible of Who, What, Where, and When, the system will apply a Secondary Analysis 114 of this data against rules in its system. The rules may include Documentation and Analysis Field Requirements 160. As shown in FIG. 31, these requirements may be based on government regulations, agency requirements, person centered goals and objectives or other types of analysis and rules which might impact data needs.

Depending on the Analysis 114 as compared with the information of Who, What, When, and Where and with the Document and analysis field requirements a determination may be made by the system to Save 127 the data to permanent storage, to eliminate from Temp Buffer 128, or Keep in Temp Buffer 129. Each step and action is tracked and logged. Any data saved is saved to a system database.

Figure 2:
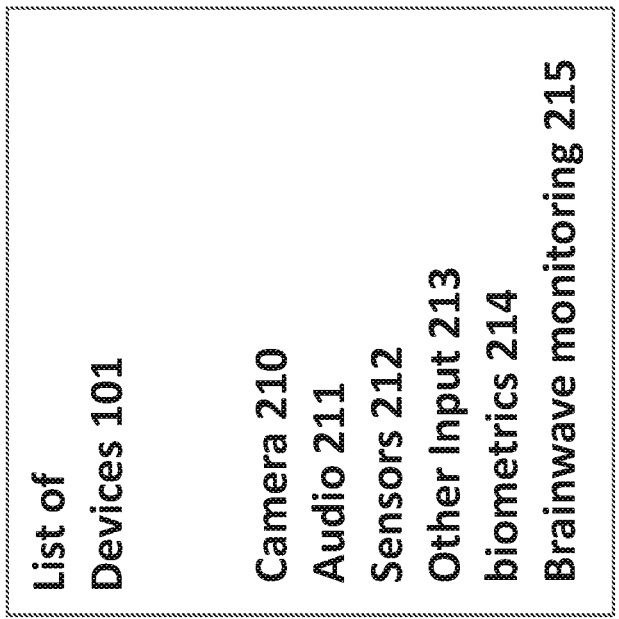
FIG. 2 illustrates a list of input devices that may be used in embodiments of the system and method of the present invention.

As shown in FIG. 2, a List of Devices 101 would transmit data to a Temporary Buffer 164.

The system may perform analysis on the data while in the buffer before it has been saved or deleted to determine what is in the video and whether it should be saved and in what quality and format. These analyses may include a Method of Identifying People in the Video 131, a method of identifying what is occurring in the video 151 and looking at items to check video against 141. Depending on the analysis of what is occurring, immediate notification based on caseloads and access 171 might be appropriate. After the system analysis there will be a decision to store data 181 with a level of quality 182 and type of storage 183. Storage is logged 191, may be tracked 192 and may be accessed by caseload 193 as appropriate.

An agency, individual, guardian, government entity or other involved entity might have an interest in having video, audio, 3D, sensory or other accurate representation of events as requirements for data collection.

FIG. 31 shows that part of the requirements for data collection may be based on the Proof of Service Delivery 225 and Proof for Billing 120. Data may be needed on service delivery such as data for the person who asked questions to the individuals or the detailed information about the approaches taken at the time of providing supports to the individual. This information may be needed to prove that the appropriate services have been provided. The proof of service delivery may also be needed for the services that need to be billed. Using this information billing data is generated which may be needed to prove that services have been appropriately administered and may be submitted as claims to be billed for. These are government, insurance reimbursement, corporate reimbursement or other reimbursements that are issued based on proof of proper service delivery. Objectives for the proof of service delivery may include reduction in fraud, government funding requirements and care and support requirements.

These data points may include audio, video, and other forms of data as shown on Data Obtained through Multiple Modes 911. Requirements may include having video or audio on certain activities. The activities recorded for video may include walking, turning around, facial movements, eye movements, running, raising of an arm, and eating. The audio recorded activities might include counting numbers, pronouncing names, vocalizations, breath sounds and answering to questions. This may also help create comparative points for data analysis.

Other Information Requirements 130 shows that part of the requirements for data collection may be based on requirements or objectives of the agency which provides services to an individual. The agency may have goals which include staff oversight, proof of service delivery, or efficient use of resources. There may be certain forms with specific data points for which information may need to be collected to maintain compliance with the agency policies. In one embodiment, the forms and data requirements may be established by various entities or people other than the individual but the data collected against these data requirements may be directly from an individual.

Funding Agency Requirements 127 shows that a funding agency may have information requirements. These may include proof of service delivery, outcomes, time, location, progress towards achieving a goal and individual satisfaction. The funding agency might require proof that is similar to or separate from billing requirements. In many cases there are separate state, federal, governments, private, non-profit or other organizational agencies which may provide funding. There may be data and information required by these funding agencies. In one embodiment, the forms and data requirements may be established by funding agencies, but the data collected against these requirements may be obtained directly from an individual.

There are a number of reasons this might be of interest. These could include the desire to prove to a government entity proof of service delivery, the desire to prove that abuse or neglect may or may not have occurred, the desire to show that an individual met his daily goals or objectives, the desire to learn from a history of actual events to better create a personalized plan for individuals, the desire to prove that staff members may or may not be accurately doing their job including perhaps the ability that a staff member is innocent or guilty of charges, and other objectives. Having a video representation of events which occurred which may not be manipulated or edited or otherwise tampered or adjusted by a staff member, agency or individual may help achieve the goal of have a record of proof. The data would be created by Devices Deployed at various locations based on different criteria established by activities, staff, individuals, governments and others. The devices may have preset levels of quality, bandwidth and compression. These levels of quality, bandwidth and compression may change over time based on analysis of what has occurred. The location may be based on fixed criteria such as a desire to have the possibility of a record of anything that occurs in a specific location. This may be because that location has had previous problems, has the potential for problems or might be a place where documentation is may be needed for proof of service delivery or other reasons.

The device location may be based on an individual's goals or activities. The camera or device may be placed on an individual as part of an effort to establish what they are doing or seeing. In fact a series of cameras may be on an individual to provide a 360 degree view of their activities and interactions.

The device location may be on the staff member for an individual. This may be to show that the staff member has performed certain activities for proof of service delivery, could be helpful to prove or disprove claims of abuse and neglect or other reasons.

The device location may be triggered by an activity or by the system. There could be preset cameras or other devices which are turned on or off based on actual events and analysis which have occurred.

One reason to limit the amount of cameras is to limit the amount of bandwidth and buffer required if there is a low expectation of need of video from a given camera.

There may be multiple types of data input sources. These may include a person-worn device, a device in a location and Alternate Input Sources.

The data in the buffer is transmitted over internet or other lines. The data may be sent to a central server or temporary buffer or RAM which serves as a Temporary Buffer Device. The data should be at an independent location not under the control of the individual, staff or agency involved in the activities in the video. The Temporary Buffer Device stores a record that it was receiving data from a given device and location. This information is logged and able to be tracked. The actual data to be saved is determined after a preset or variable period of time. The Temporary Buffer Device should have backup power and perhaps a backup Temporary Buffer Device to ensure the Temporary Data is not lost due to a problem at the Temporary Buffer Device.

The system may receive notice that the Temporary Data Device had received Temporary Data. The system may identify or attempt to identify the people in the video using Methods of Identifying People in the Video 131 and identifying what is occurring in the video 151.

Based on its identification of the people in the video 131, the system may have access to that person's individual goals and objectives, history, service documentation needs, proof of service delivery requirements and other person centered documentation objectives and requirements 143. The system may then determine based on person centered documentation requirements the events which had occurred what sort of saving should occur to the data that is Temporary Data. The system may direct the Temporary Data to be stored in one or more of a variety of formats.

The system may also determine based on the combination of what occurred plus the individual identified that data should be stored in a certain quality of storage for a period of time after that event had occurred. The system may also determine based on the combination of what had occurred to store other data currently in Temporary data from the same Device as well as storing data from other devices in the list of devices.

Based on the combination of the identification of people in the video, what occurred and checking against person centered information requirements, the system may determine that additional devices should be turned on, that storage should be captured from additional devices, that notifications should be made to appropriate people or entities, that data should be transferred at higher or lower quality from the device and other possible actions.

Based on its identification of what is occurring in the video the system may review and compare that data against agency based items to check video against. The system may have access to that agency's policies, goals and objectives, history, service documentation needs, proof of service delivery requirements and agency objectives and requirements 143. The system may then determine based on agency documentation requirements the events which had occurred what sort of saving should occur to the data that is Temporary Data. The system may direct the Temporary Data to be stored in one or more of a variety of formats.

The system may also determine based on the combination of what occurred plus the agency requirements that data should be stored in a certain quality of storage for a period of time after that event had occurred. The system may also determine based on the combination of what had occurred to store other data currently in Temporary data from the same Device as well as storing data from other devices in the list of devices.

Based on the combination of the identification of people in the video, what occurred and checking against person centered information requirements, the system could determine that additional devices should be turned on, that storage should be captured from additional devices, that notifications should be made to appropriate people or entities, that data should be transferred at higher or lower quality from the device and other possible actions.

Figure 24:
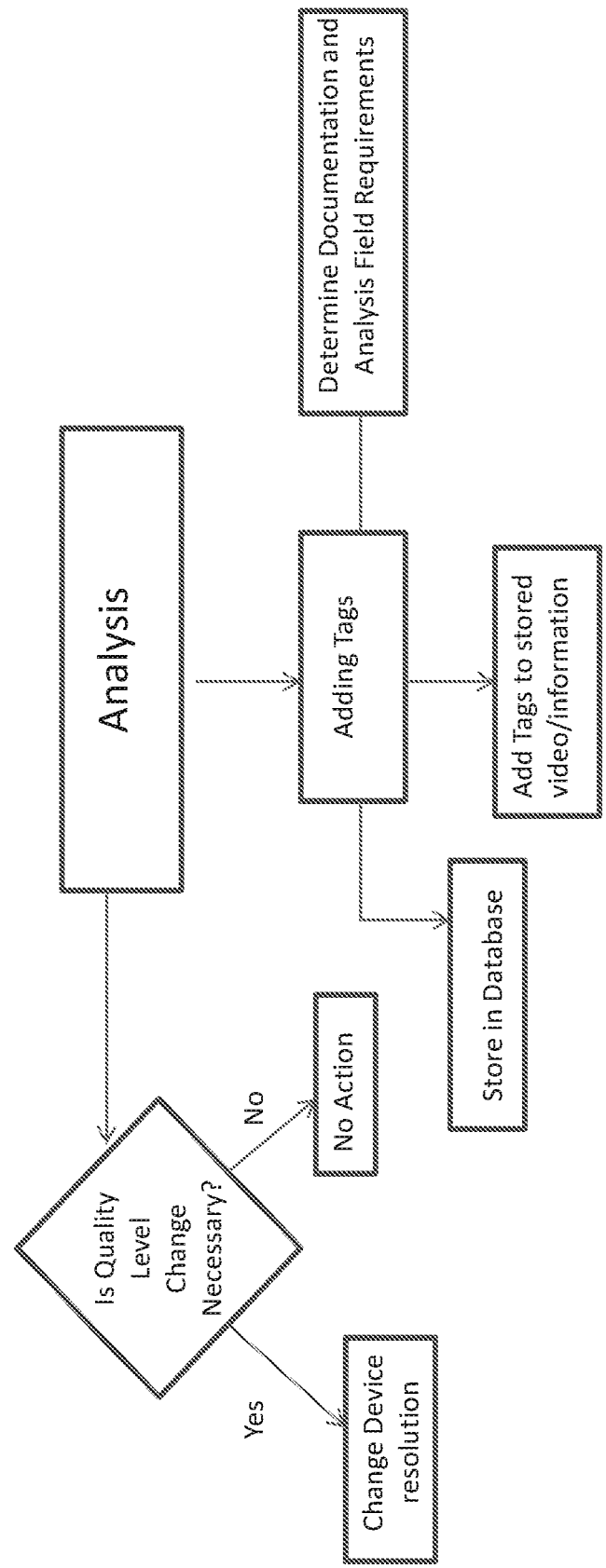
FIG. 24 illustrates how analysis by embodiments of the system and method of the present invention may include a change in storage quality level or adding tags to the data.

As illustrated in FIG. 24, the system may combine its analysis of information against person centered requirements, items which are agency based requirements, general society-based requirements and other items to check data against to determine what level and quality of storage. Any data stored could only be accessed by people with the proper roles and caseloads.

The system may first attempt to identify the people in the video 131 based on information including the location of the device and then attempt to identify what is occurring in the video 151 based on the previous identification of people in the video as well as other information.

Alternatively the system may first attempt to identify what is occurring in the video. There could be a situation where the people may not be identified but the activity is known. The system could compare the activities against items to check against based on society general requirements and also agency based requirements for the device location.

Figure 27:
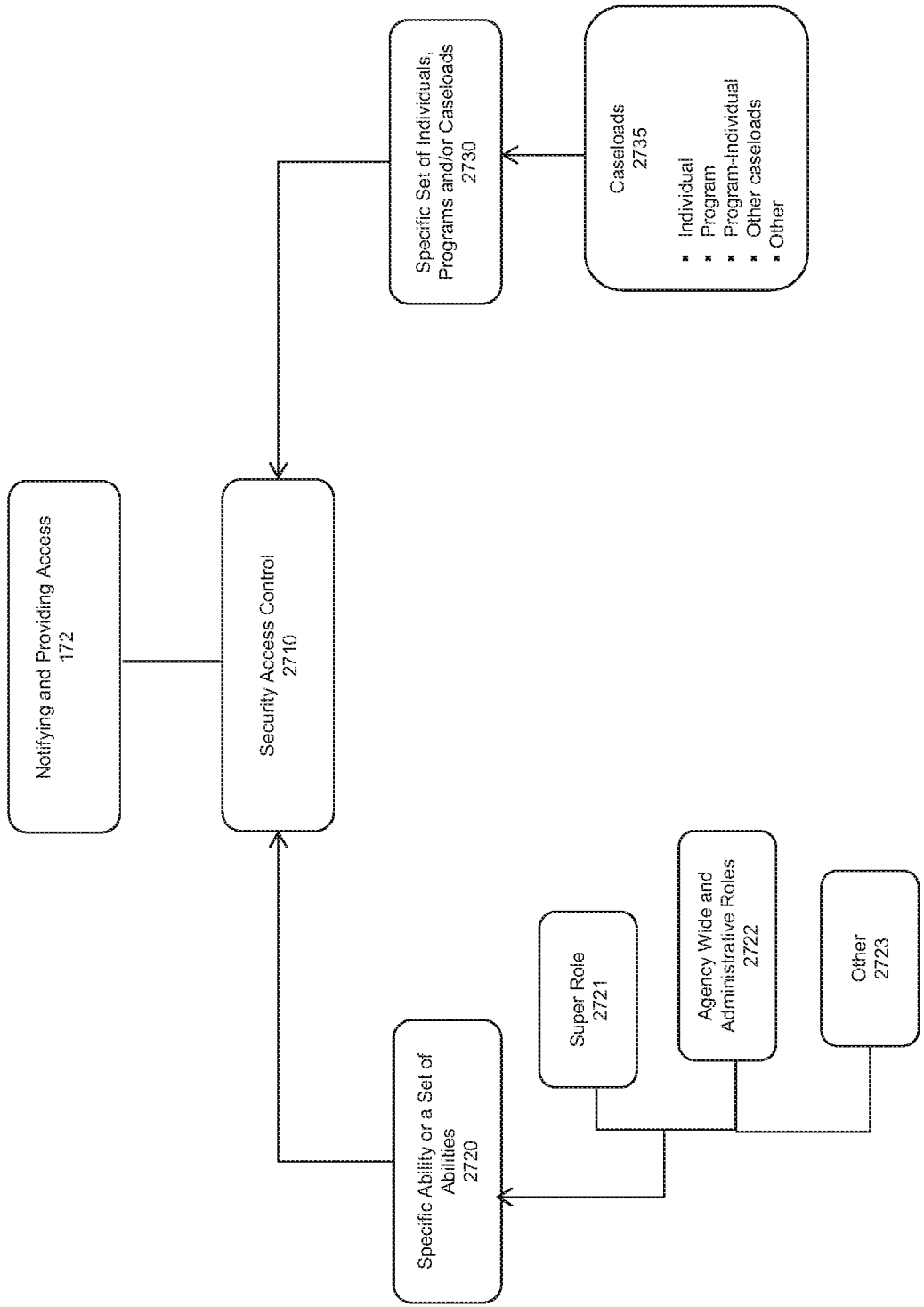
FIG. 27 illustrates how embodiments of the system and method of the present invention control access to information is based on caseload(s) and defined access roles.
Figure 27A:
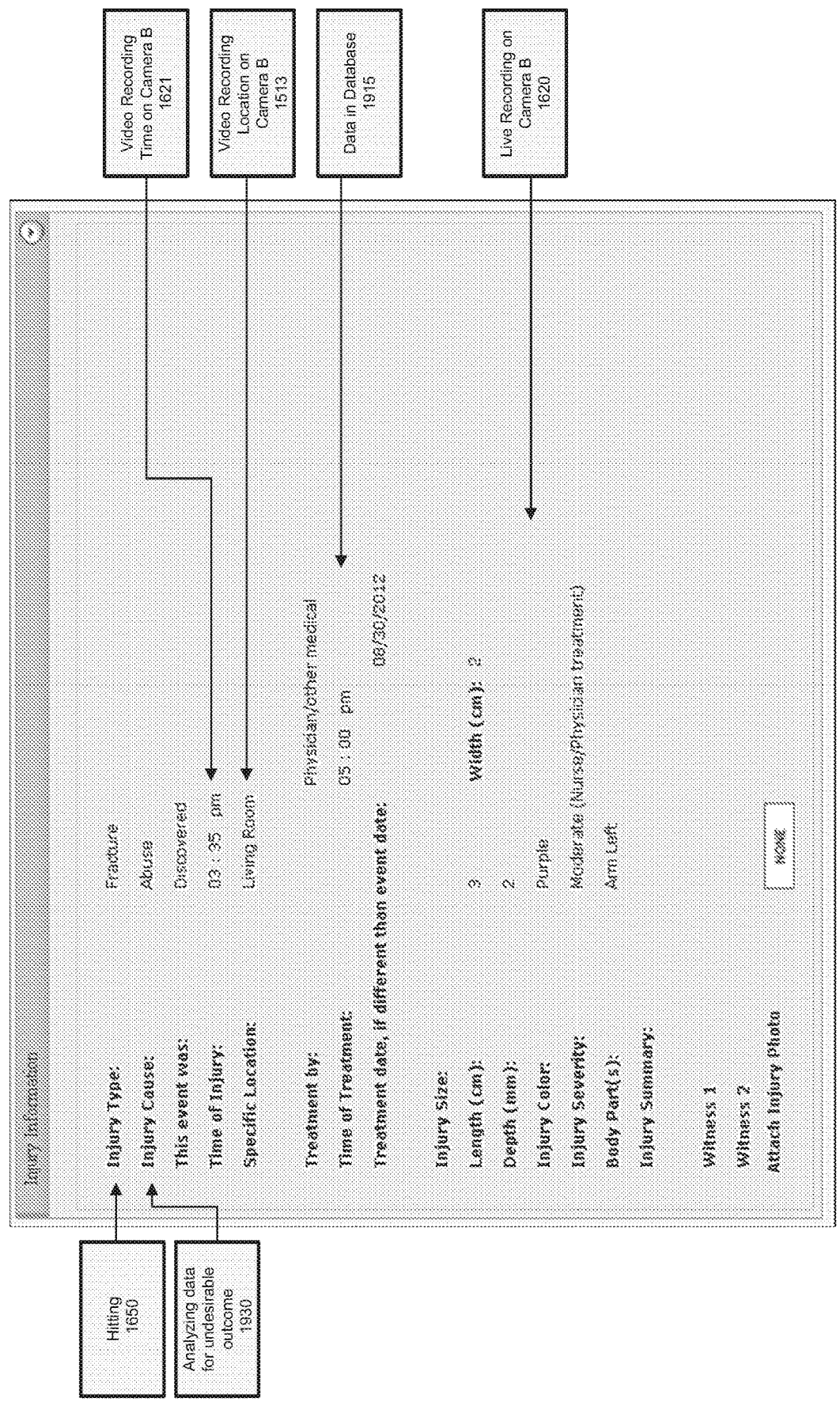
FIG. 27A illustrates an injury information screen view that may be generated by embodiments of the system and method of the present invention.

As shown by reference 911 in U.S. Pat. No. 8,281,370, data may be stored in the system's storage array. As illustrated in FIG. 27, access to information is based on caseload (s) and defined access roles. The documentation may include the information on caseloads, tracking, storage, and tagging as discussed in U.S. Pat. No. 8,281,370, including but not limited to the discussion at Col. 5, line 21-col. 7, line 32.

Initial Inquiries

When an individual is first in either the system or in an Entity Providing Service there is often a relatively limited amount of Person-Centered Data about an individual. In that case the system may create initial queries or approaches to gathering information based on more generic approaches to information based on typical information for other people with the same condition or set of displaying conditions or diagnoses. As additional information is gathered through the process, the queries may be tailored more to Individual based on their specific information and data. There may be a continual process of reviewing the analysis and queries which lead to more information and more analysis.

System Generated Inquiries show that the system then processes the answers and attempts to generate the next query, intervention or next request for information. In some cases there might be preset templates which generally walk through a set of inquiries or queries.

Mapping Information into Forms 165 shows that the system analyzes the information which has been collected using various methods and makes the best match it may to fill out required forms. The system may still store and maintain all of the pieces of data which went into trying to match the data requirements.

Notifying and Providing Access 172 shows that the system may notify staff, guardian, government officials and other people with appropriate access privileges about the information on individuals generated on forms and data fields 1940. The system may also provide proper access on individuals to staff authorized to view their information through appropriate caseloads and super roles.

Figure 28:
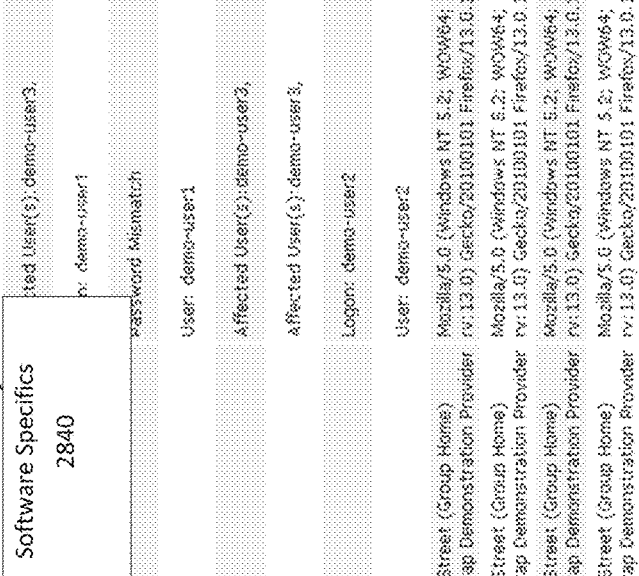
FIG. 28 illustrates an activity tracking screen view that may be generated by embodiments of the system and method of the present invention.
Figure 29:
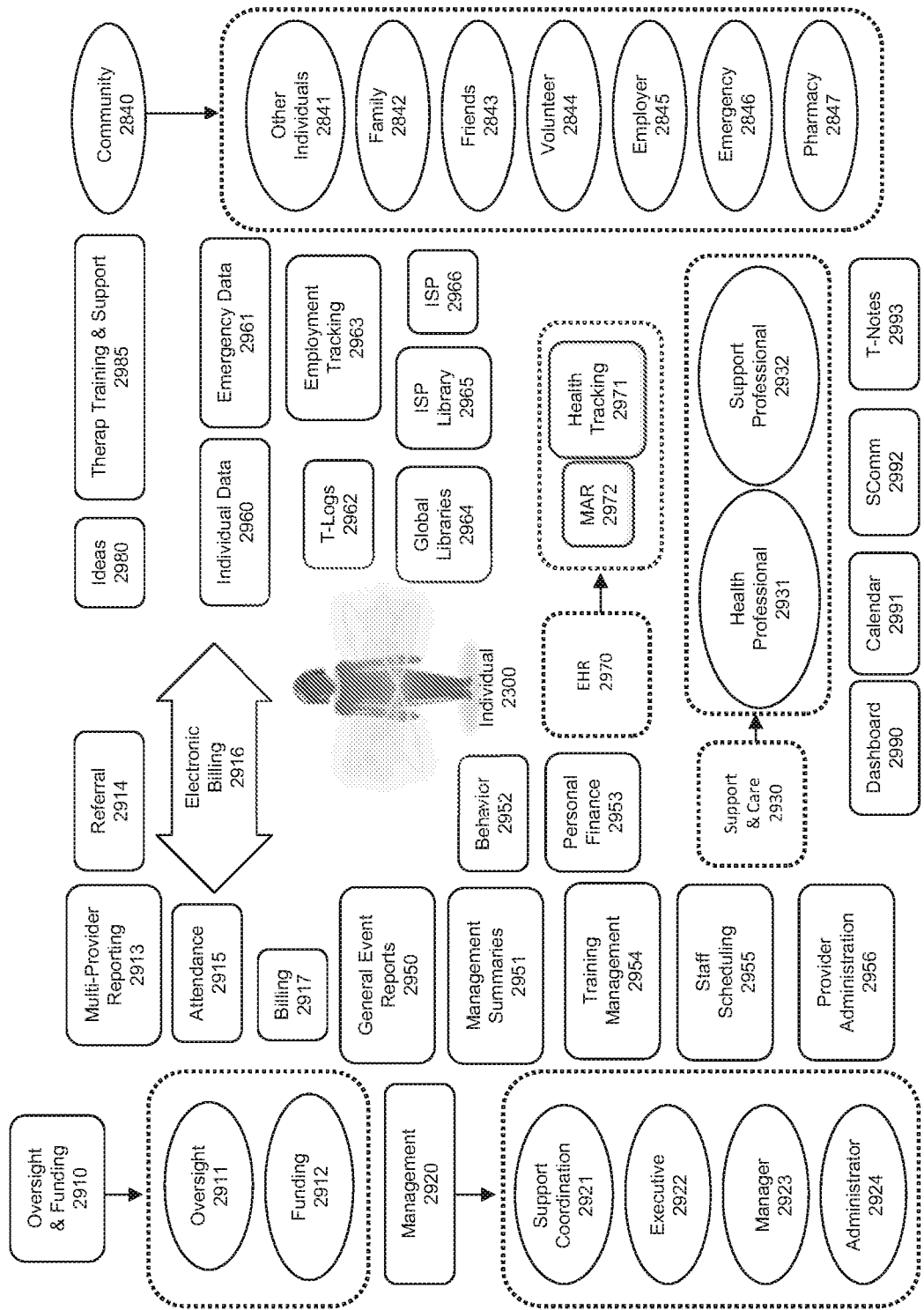
FIG. 29 illustrates an overview of a support and treatment environment relating to an individual under care.
Figure 29A:
FIG. 29A illustrates a suspected physical abuse screen view that may be generated by embodiments of the system and method of the present invention.
Figure 30:
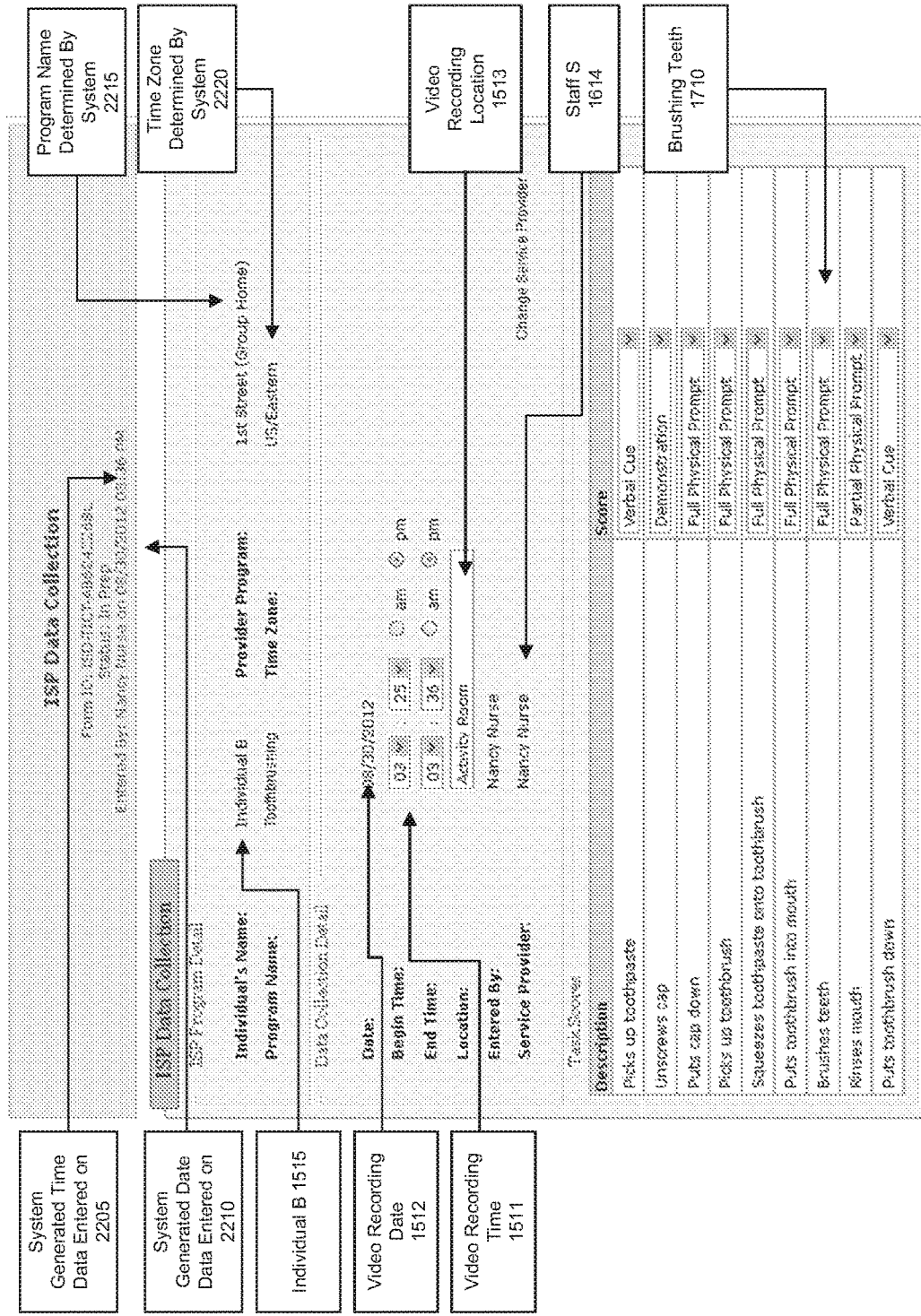
FIG. 30 illustrates a screen view of a form with collected data that may be generated by embodiments of the system and method of the present invention.

Monitoring and Analysis of Information shows that the data stored into the system is monitored and analyzed. The analysis of data received using different methods may be performed by the system or by human beings. In each case access is defined by caseload and role. As illustrated in FIG. 28, activity is monitored and logged in an activity tracking log 2810.

The system may use algorithms and formulas to interpret the intent of the individual's information. This information may be checked against previous information provided by the individual and mapping may be performed for consistency, errors, possible fraud, possible abuse and neglect, and other issues which might arise.

Once data has been viewed by the system as part of this analysis, it may be recorded as 'viewed' or 'read' or with some other appropriate annotation in the database to indicate that the data or information has been viewed.

The system may have multiple accounts based on different caseloads and super-roles to indicate when it has viewed or acted on information at the time of the viewing.

For example, the set of caseloads and roles of the system might replicate the roles that an individual staff, guardian or other human might have. Then the system may perform certain analysis to detect fraud, abuse and health assessments, or other issues. Since the system may view these pieces of data or information, there is real time documentation that an analysis had been performed according to a certain set of rules or protocols. Only people with proper access to those caseloads and roles would be able to see that the system accessed that information and performed that analysis.

People with appropriate caseloads may be able to provide necessary information which may differ from information provided by other staff under different circumstances. The system may store this information for reference and analysis in order to generate answers and fill out forms. Stored data may be available for review with appropriate caseloads and access. If information from multiple users for an individual show a disagreement on a set of facts, the system may analyze the data combined with other information it has from sources including external sources and data collected in the system. The system may make a determination on the most likely correct set of facts. The system may also reanalyze previous facts in the system in light of having to interpret or remap data in this instance as multiple people may have had disagreement on information. This could be an indication that other data and information may need to be reanalyzed. If data is re-interpreted, that could mean that forms may need to be changed or other processes and procedures may need to be revisited. The system may determine if decisions were based on a given set of information.

Many agencies are required under HIPAA, HITECH, funding requirements, or state or federal laws or policies of the Entity Providing Support 250, to perform certain analyses within certain periods. Having these analyses performed by system acting and documenting like a human being may allow proof that these analyses were documented. The system may function as an electronic staff member, robot, drone or other form of automated method to carry out tasks and supplement or replace an individual staff member or other person. It may not be sufficient to show that the information was in the system. It may be required to document that the analysis was performed by an entity (in this case a system rather than a person) with sufficient rights under roles and caseloads to do the analysis.

Depending on caseload and role, the system also has the ability to reanalyze and reinterpret previous mapping and interpretations of past data and information as shown in Reanalyzing old data based on new data. The system might have the option to take other individuals experiences into account or if the system notices any inconsistencies or changes required, the system may add a follow-up or changed comment based on the new analysis. The system may also flag or provide notification to people who had a proper caseload and role for the change.

Reinterpreting information and mapping 195 shows that after comparing and reanalyzing the responses of the individuals received under different circumstances, the system might change the interpretation of data while the original raw data and past information still available in the system. Since all the information is stored, the system may reanalyze the data collected using different methods and generate forms with the data having the best possible match.

The system may reanalyze the need for information if there is a mismatch after comparing old data based on new information. The system may also reanalyze the goals and objectives of the Individual and data collected from the Individual or the surroundings of the Individual.

Currently and historically analysis may occur by individuals or committees (such as agency human rights committees, risk management committees or incident review committees) which meet periodically to review information. Under this system, the analysis could occur in real time by the system directly from information provided by an individual and the environment. This accomplishes several objectives. The information is gathered directly from the individual with a cognitive disability; multiple types of information and data may be used in the calculation; and information may be saved so the data is stored in a real time manner, so even if an interpretation is changed later, the data was still created in real time. There is also the ability to create caseloads which are theoretically possible but could be quite difficult to create in real time.

As indicated in Submitting information to government and other entities, government and other entities might want the ability to view data across multiple agencies. A state director or state head of nursing or other senior positions which have access to data across organizations could want the ability to have analysis done. This is historically time consuming and resource intensive. With this system, the analysis could be possible in a manner consistent with maintaining the privacy of data and respect for the individuals. By the system performing the analysis with caseloads and roles ranging from access to one individual to having access to up to all individuals in the system, it is possible to determine information including fraud, abuse and neglect, and other types of objectives. The system may generate forms based on the analysis of all the information stored in the database. It may then be able to submit these forms to governments and other entities.

In addition, because the system is aware of staff and others caseloads, the system has the ability to notify proper people who should be made aware of the situation as shown in Notifying and Providing Access 172. When the analysis is done by staff, such notification of issues may only occur when the care provider takes the time to do so. Even when staff has time and effort to provide notification, there may also be other issues such as confusion on who should be notified for a given situation.

The system may also determine who should have known about a situation. Because of the access to caseload and role information in the system, the system may allow agencies to determine who might have had access to information to make a determination and also help prove who might not have had the information. This allows for a higher level of accountability on the part of service providers than exists currently.

There are many cases where staff, guardians, administrators or governments is accused of knowing certain information and not acting on information that they were aware of. This system may enable an Entity Providing Support 250 to establish the system under proxy caseloads and roles to see what information they might have known based on the information they could have had access to.

As shown in FIG. 2, the list of devices 101 that the system may interact with may vary by agency or installation. The devices may include various functionalities. The functionality may be expected to evolve as new technology is introduced. The list of devices may include camera 210, audio 211, sensors 212 other input devices 213 biometrics 214 brainwave monitoring 215 cellphone 216, computers, PDA's, Laptops, tablets, and other commercially available devices.

The system may take information or data straight from the device without saving or storing any information on the device. Data may have a link to bandwidth, internet, access interface or other method of having data reach the Temporary Data Storage Device without having been saving on an interim device.

As shown in FIG. 8, List of Range of Methods and Qualities of Storage 121, the system may receive and store data in a variety of ways. The system may not store data in a higher resolution than information is initially received. For example if information is received in X number of bits, X number of bits would be the maximum storage that may be saved. Information or pictures may be stored in lower formats. For example a High Definition quality video may be saved and stored in both high definition and low definition (among other choices). A video may be saved as a single picture in a preset or to be determined time frame. A video may be saved as a video without audio or as audio without a picture. A video or picture may be saved as a portion of the screen. For example if there was a video at a park with many people in the background in order to reduce storage costs perhaps the bottom right quadrant of the video could be saved which may cover the relevant documentation requirements, yet reduce the cost of storage.

Figure 16:
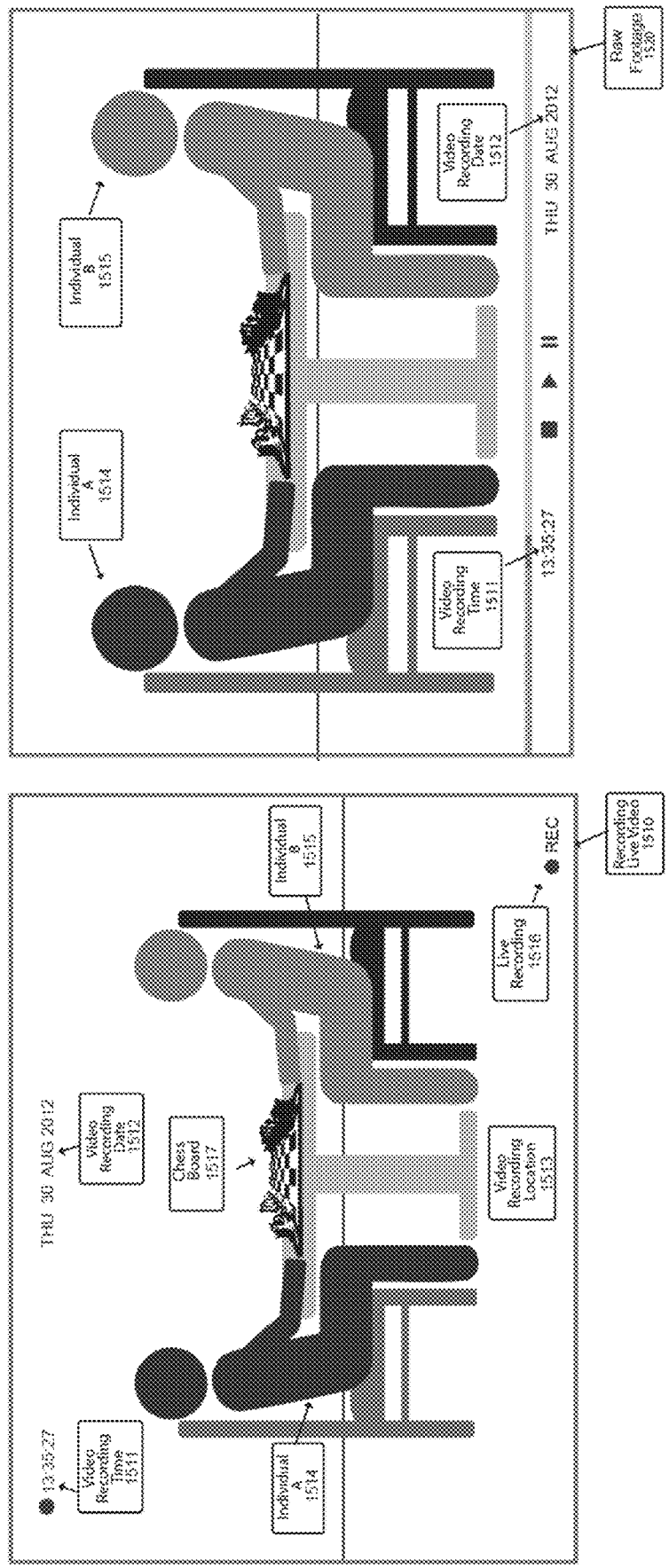
FIG. 16 illustrates an example of two individuals in a video recording.

As illustrated in FIG. 20, a the List of Devices 101 may be in a variety of locations there will be a variety of Methods of Identifying People in the Video 131. These may include one method or a Combination of Methods 421. A combination of methods means that more than one method contributed to the determination of who was in the video. There may also be a determination that for a given person in the video it is unclear who the person might be. There may be a situation where the system gives instructions and collect data on more than one possible person if there were uncertainty over who a specific person in the video is. There may be multiple people in the video. It is possible that one or more people may be identified with a high degree of certainty and that one or more people may be identified with a low degree of certainty and that one or more people might not be able to be identified. Holding the data in a Temporary Data might permit the identification of a person at a later time. For example if individual A in FIG. 16 is facing the camera and may be identified and Individual B is facing away from the camera, at a later time with continuous video coverage it might be possible to identify individual B.

The system may have the ability to use previous documentation about an individual to improve the accuracy of having the correct person identified. The system may have access to previous information about an individual which helps assess who the person is. The system may know who has been in a given location in previous periods. The system may have information about scheduled expectations include what staff has been scheduled and what activity is expected to occur at a given location. These may enable the system to check biometrics, photos, voice, movements, against an expected set of individuals.

Figure 25:
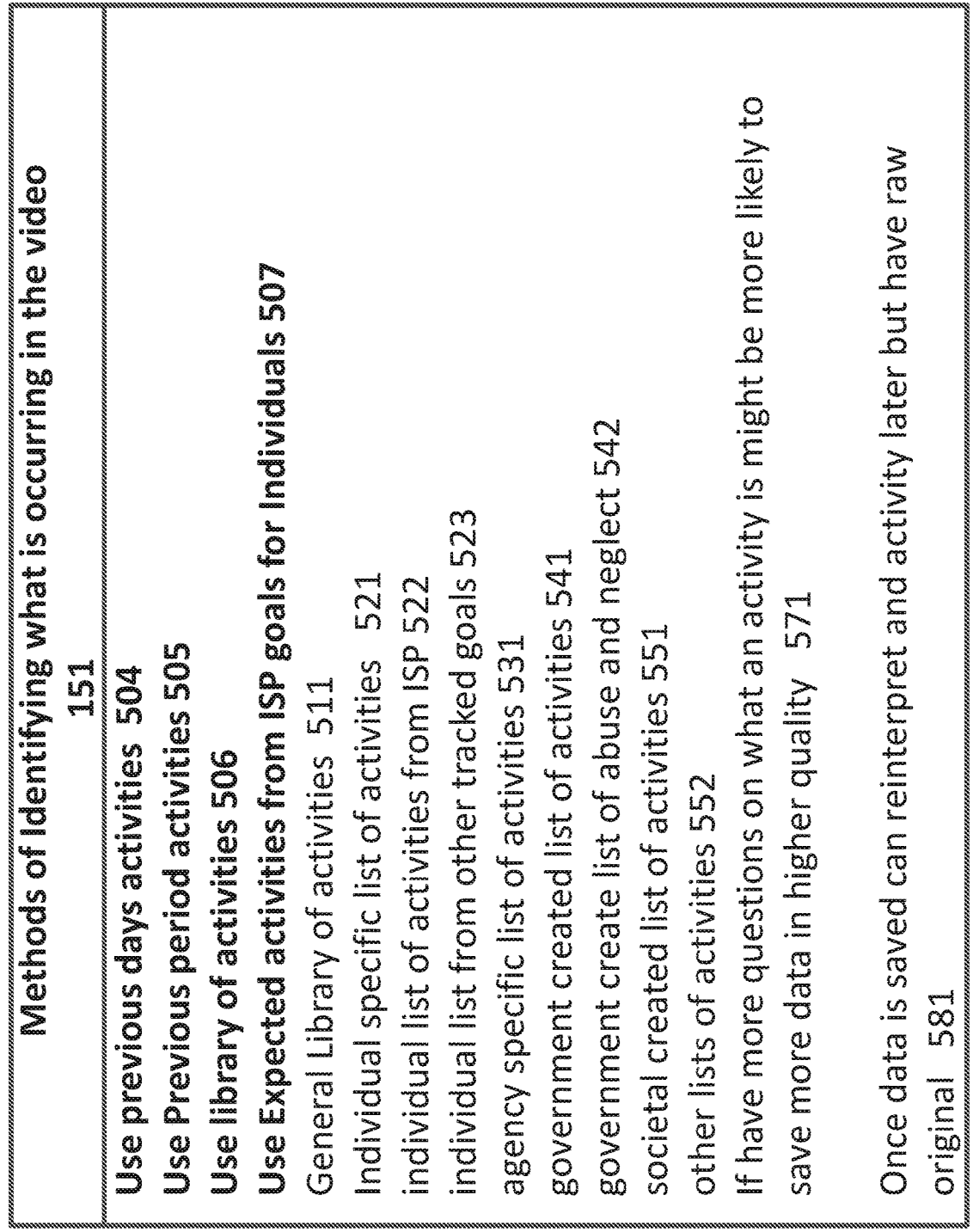
FIG. 25 illustrates methods of identifying what is occurring in a video that may be employed by embodiments of the system and method of the present invention.
Figure 25A:
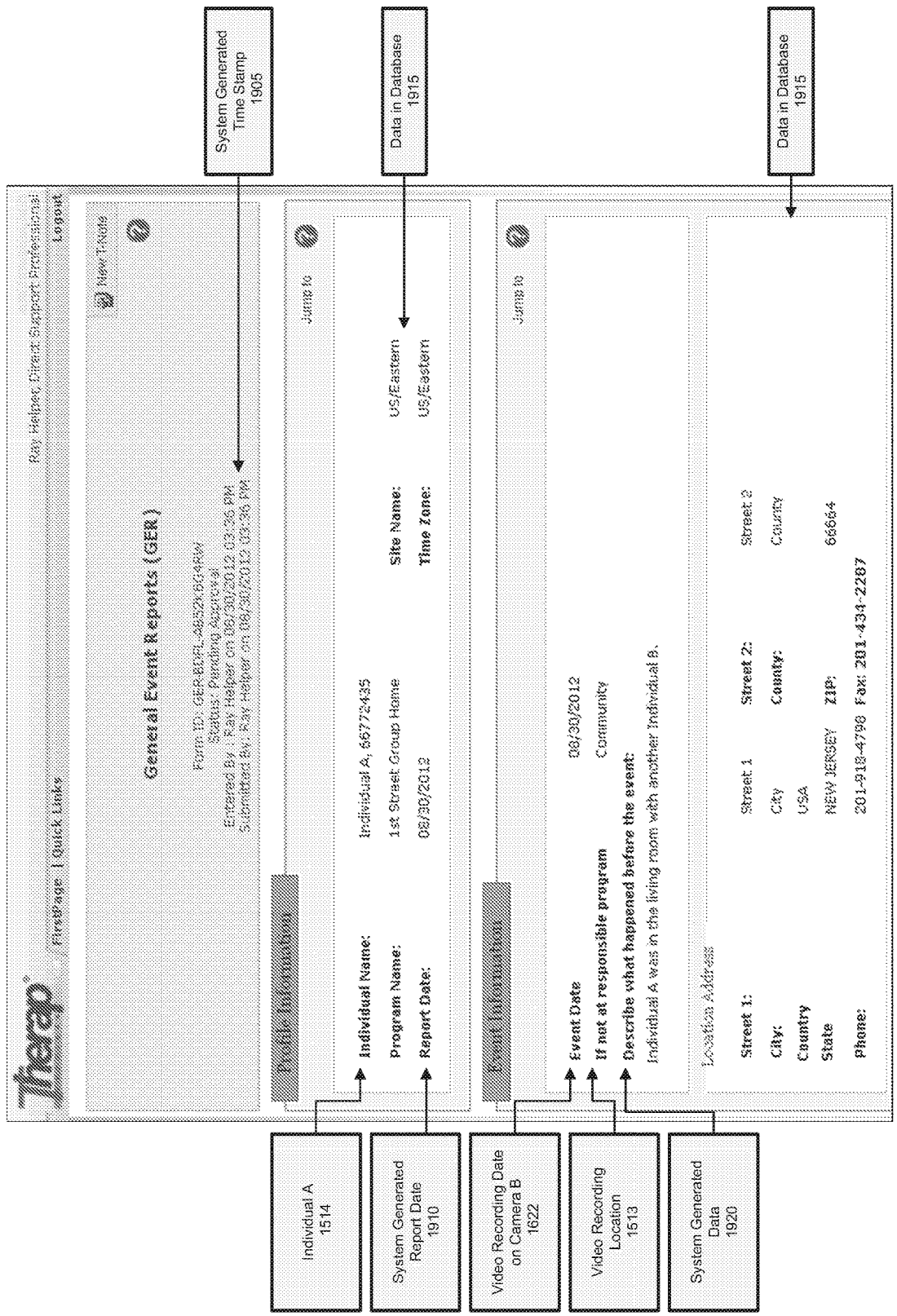
FIG. 25A illustrates an event report screen view that may be generated by embodiments of the system and method of the present invention.

As shown in FIG. 25, the system has various methods of identifying what is occurring in the video 501. The system may need to distinguish from a variety of activities which may or may not have occurred which may or may not need to be saved in various formats. These activities or actions may include actions such as running, walking, eating, which may have general societal definitions as well as interpretation of individual specific actions which may be tied to individual person centered goals which for example might be someone having independence to walk across a street and the activity may not be only walking across a street but may be walking across the street as part of a person centered program.

There may or may not be more than one activity going on at one time. For example, an individual may cook chicken for dinner and the activities may include eating dinner, having a staff oversee the individual, and the individual eating chicken. Each of these may require different needs for documentation and saving.

One method is to look at the activities from previous Period Activities 505. The system would have the guidance of what had occurred in previous days. For example if a certain activity had occurred at the same location or with the same individuals or at the same device in a previous time period, this would be something to track against in determining what has occurred.

There may be a Library of Activities 506. The system may have a general library of activities which video may be checked against. This may include activities defined by the system, by users of the system or lists generated from other sources including the internet, government agencies and other externally generated definitions.

The library of activities may be tied to the location of the device, to one or more individuals identified, to an agency monitoring the device, to government regulations or to other lists. For example, a Device that was in the kitchen could have a set activity to monitor more closely a certain knife which could be dangerous or a source of abuse and neglect.

There may be a specific list of activities from Person Centered Goals for Individual 507. These goals may be detailed items such as a tooth brushing program or a laundry training program. Person Centered Goals for Individual 507 are discussed in patent application Ser. No. 13/675,440 filed Nov. 13, 2012.

There may be an Individual specific list of activities 521. Once an individual is identified, there may be specific activities which that individual engages in. This list may be created on a specific form of Individual List of Activities 521 to be monitored or documented. An alternate method of creating the list would be from documentation requirements in person centered or other programs such as behavioral plans, individual plans of protection, HAB plans, and other documentation requirements or objectives.

There may be an Agency Specific List of Activities 531. Agencies would be able to enter specific activities that they track or define for documentation and support requirements. For example, different agencies could have different methods of interpreting and naming restraints or behaviors.

There may be a Government Created List of Activities 541. The government or other supervising jurisdiction could require documentation of certain types of events or activities. These activities could be in a list to be checked against.

There may be a Government Created List of Abuse and Neglect 542. There may be specific types of activities which are defined as abuse and neglect. These may have separate requirements in terms of notifications or access to data. Different government entities may have different definitions for this list. There may be certain acts of neglect which might be considered the absence of an agency. For example an agency which allowed an individual with certain cognitive disabilities access to boiling water to scald them would be in neglect and that might need to be documented.

There may be other Societal Created List of Activities 551. There may be lists or combinations of video and definitions which may be entered or imported. The system may hold lists. These may be listed from the internet or other public sources.

Once data is saved in the system, it may later be reinterpreted. If there is uncertainty regarding an event the system may take actions which might include saving the temporary data, continue storing the temporary data to determine what occurred, sending a message to the device to take higher quality video, sending a message to a different device to obtain an additional angle or view or perspective on the event, or contact a staff or human being to help obtain clarification or interpretation of what has occurred.

There are many types of Items to Check Video Against. These items may include items which involve Proof of Service Delivery, ISP Goals, Abuse and Neglect, Person Specific Neglect Issues, Staff Specific Neglect Issues, Positive Goals, Government List of Activities to Document or Other Items.

Uses

There are many situations in which the system may be useful. For example, school administrators may use the invention to monitor children. The invention may check attendance either at the beginning, middle, or end of the school day. It may also monitor bullying or taunting to find out what happened between students and what happened immediately after. It could also then scan data with a temporary status to look for earlier interactions between the children and save the interactions relating to the students involved in the fighting. It may also, store or save, turn on additional cameras, or notify adults when a student is bleeding, fighting, injured, suffering from trauma, having an allergic reaction or consuming potential allergy causing foods and substances. It may also recognize serious events such as use of Epi-Pens, seizures and other medical problems. It may monitor teachers for improper behavior or record and alert the presence of intruders in the school. In all of these situations the invention may also review saved or temporary data for related events, such as those leading up to the original event, and save those events accordingly. It should be noted that in some situations may need to be carefully distinguished, such as football tackling versus fighting.

Similar to applications discussed above, data involving school behavior may require caseloads to view. For example, in some embodiments, parents may only see information about their own child. It should also be noted that the inability to delete information may help in situations where, for example, students or communities do not trust the school administrators.

Consider the example of person A making a first on the playground. The invention looks at the previous times person A made a first and any correlations between those instances and the current instance. It will also look at who or what is near A and A's facial expression. It may compare this data to previous instances and determined what happened in the instances with the same data i.e. where A made a first with the same person around and the same facial expression. The invention will consider activity A is supposed to engage in. It will possibly alert an available adult such as a teacher or supervisor, and possibly instruct other nearby cameras to record A and his surrounding area. The invention will then analyze the behavior plan for A and see under what circumstances the present behavior is likely to be problematic. It will check for rules regarding recording such as "if there is a first in the video, store the video." If the particular embodiment of the invention is capable of lip reading, it will attempt to analyze lip movement and determine what is said. If the particular embodiment is able to collect and analyze audio, it will listen to context of A's present conversation and determine if a threat has been made.

If person A then hits person B, video of this interaction will, depending on the setting on the embodiment, most likely be saved. Consider though that A and B are pretending to be boxers or wrestlers. In that situation, the invention might save only enough information to make the nonviolent nature of the act clear. It will thus save less information than when violence is present or thought to be present and will not inform adults. It might also still check the history and the items discussed above to find correlations and potential problems among interactions between A and B.

The present invention might also be used in prisons to monitor fights and injuries. This may be useful in areas where guards are not such as bathrooms. It is also useful with police interactions such as determining stop and frisk or police misconduct. It helps in situations where people are worried that authorities are manipulating data and videos too. It also is helpful in monitoring builds, vehicles, and movable items. The invention also accommodates situations where a person might not want to save data, such as if regulations will change.

It should be noted that the invention may require libraries of general activities to check against, likely those of egregious behavior such as hitting, punching, biting, pulling hair etc. It also may need a library of individual specific videos to check data against.

Features of Embodiments of the Invention

Embodiments of the invention may include one or more of the following:

1. A process of Saving Video and other data based on rules and results without deleting data that is not needed to be saved.

2. A process of determining quality/definition of storage requirements without deleting data.

3. A process of utilizing secure person-centered data to determine what data and information should be saved and stored without having any data deleted.

4. A process of notifying people based on caseloads and access about information in a buffer prior to the need to make a decision about saving the data.

5. A process of using person-centered individual goals to determine which cameras and in what quality data should be taken.

6. A process of storing data in multiple records based on caseloads so only portion of data is saved in an individual's files.

7. A process of using data requirements created from external requirements (government/surveyors) and based on caseloads of different staff/persons/agencies, across multiple organizations, which would not be available to any single individual, and sending requirements to one or more cameras/devices and then storing data in a temporary manner until and after the fact analysis against requirements in a system may determine how and in what format data should be saved.

8. A process to automatically determine which video or audio sections or events may need to be reviewed or cleared for storage as normal or reduced HD quality, with automatic notification to review to the system for automated analysis or assigned individuals for human review.

The invention claimed is:

1. A system for recording healthcare information of an individual under care based on properties of the information without deleting data, the system comprising:
   a device for capturing person centered data relating to an individual, and configured to transmit said data and a signal identifying said device;
   a memory for storing rules relating to said device;
   a buffer;
   a database; and
   a processor adapted to:
      receive said device identification signal and said data;
      retrieve said rules from said memory;
      determine, based on said rules, whether:
         said data is to be stored in said database; or
         said data is to be stored in said buffer;
      perform an analysis of said data to determine, based on content of said data:
         the location of the device;
         the time that the data was recorded;
         whether the individual recorded is identified as the individual under care;
         the activity performed by the individual;
      determine, based on said rules, and said analysis, whether:
         said analyzed data is to be stored in said database; or
         said analyzed data is to be eliminated from said buffer; and
      store said analyzed data in said database, if so determined, or eliminate said data from said buffer, if so determined.

2. The system of claim 1 wherein said data relates to goals of the individual under care.

3. The system of claim 2 wherein said data relates to achievement of said goals of the individual under care.

4. The system of claim 1 wherein said data relates to outcomes relating to the individual under care.

5. The system of claim 4 wherein said data relates to undesirable outcomes.

6. The system of claim 4 wherein said data relates to proof of said outcomes.

7. The system of claim 1 wherein said data relates to errors regarding the individual under care.

8. The system of claim 7 wherein said data relates to medication errors.

9. The system of claim 1 wherein said device is also configured to capture non-person centered public data, and said data includes said person-centered data and said non-person centered public data.

10. The system of claim 1 wherein said data is Protected Health Information (PHI).

11. A method for recording healthcare information of an individual under care based on properties of the information without deleting data, the system comprising:
   capturing, by a device, person centered data relating to an individual;
   transmitting, by said device, a signal identifying said device;
   storing, by a memory, rules relating to said device;
   receiving, by a processor, said device identification signal and said data;
   retrieving, by said processor, said rules from said memory;
   determining, by said processor, based on said rules, whether:
      said data is to be stored in a database; or
      said data is to be stored in a buffer;
   if so determined, storing said data in said database, or if so determined, storing said data in said buffer;
   if said data is stored in said buffer, performing, by said processor, an analysis of said data to determine, based on content of said data:
      the location of the device;
      the time that the data was recorded;
      whether the individual recorded is identified as the individual under care;
      the activity performed by the individual;

determining, by said processor, based on said rules and said analysis, whether:
said analyzed data is to be stored in said database; or
said analyzed data is to be eliminated from said buffer; and
if so determined, storing said analyzed data in said database, or
if so determined, eliminating said data from said buffer.

12. The method of claim 11 wherein said data relates to goals of the individual under care.

13. The method of claim 12 wherein said data relates to achievement of said goals of the individual under care.

14. The method of claim 11 wherein said data relates to outcomes relating to the individual under care.

15. The method of claim 14 wherein said data relates to undesirable outcomes.

16. The method of claim 14 wherein said data relates to proof of said outcomes.

17. The method of claim 11 wherein said data relates to errors relating to the individual under care.

18. The method of claim 17 wherein the data relates to medication errors.

19. The system of claim 11 wherein said capturing step further includes capturing non-person centered public data, and said transmitted and received data includes said person-centered data and said non-person centered public data.

20. The method of claim 11 wherein said data is Protected Health Information (PHI).

* * * * *